(12) United States Patent
Mintz

(10) Patent No.: US 10,526,383 B2
(45) Date of Patent: Jan. 7, 2020

(54) GHRELIN SPLICE VARIANT FOR TREATING NEURONAL DAMAGE, NEURODEGENERATIVE DISEASE, PARKINSONS DISEASE, ALZHEIMERS DISEASE, AND/OR DEPRESSION

(71) Applicant: Liat Mintz, East Brunswick, NJ (US)

(72) Inventor: Liat Mintz, East Brunswick, NJ (US)

( * ) Notice: Subject to any disclaimer, the term of this patent is extended or adjusted under 35 U.S.C. 154(b) by 0 days.

(21) Appl. No.: 15/663,039

(22) Filed: Jul. 28, 2017

(65) Prior Publication Data

US 2017/0342117 A1 Nov. 30, 2017

Related U.S. Application Data

(62) Division of application No. 14/896,449, filed as application No. PCT/US2014/046681 on Jul. 15, 2014, now abandoned.

(60) Provisional application No. 61/846,920, filed on Jul. 16, 2013.

(51) Int. Cl.
*A61K 38/25* (2006.01)
*C07K 14/47* (2006.01)

(52) U.S. Cl.
CPC .............. *C07K 14/47* (2013.01); *A61K 38/25* (2013.01)

(58) Field of Classification Search
None
See application file for complete search history.

(56) References Cited

U.S. PATENT DOCUMENTS

| 2009/0043074 A1 | 2/2009 | Mintz |
| 2010/0216706 A1 | 8/2010 | Horvath et al. |

FOREIGN PATENT DOCUMENTS

| EP | 1506786 A1 | 2/2005 |
| EP | 2070549 A1 | 6/2009 |
| KR | 2009-0076254 A | 7/2009 |
| WO | 2007/126792 A2 | 11/2007 |

OTHER PUBLICATIONS

Gahete et al., A Novel Human Ghrelin Variant (In1-Ghrelin) and Ghrelin-O-Acyltransferase Are Overexpressed in Breast Cancer: Potential Pathophysiological Relevance, Aug. 2011, PLoS One vol. 6 ,Issue 8, e23302, 11 pages.*
Meredith et al., MPTP Mouse Models of Parkinson's Disease: An Update, (Jan. 1, 2011), Parkinsons Dis. 1(1):19-33. doi:10.3233/JPD-2011-11023.*
Benatar, M., Lost in translation: Treatment trials in the SOD1 mouse and in human ALS, 2007, Neurobiology of Disease 26:1-13 (Year: 2007).*
DiBernardo et al., Translating preclinical insights into effective human trials in ALS, 2006, Biochimica et Biophysica Acta 1762:1139-1149 (Year: 2006).*
Andrews et al., Ghrelin Promotes and Protects Nigrostriatal Dopamine Function via a UCP2-Dependent Mitochondrial Mechanism, The Journal of Neuroscience, 29(45):14057-14065 (2009).
Delikanaki-Skaribas et al., Daily Energy Expenditure, Physical Activity, and Weight Loss in Parkinson's Disease Patients, Movement Disorder Society, 24(5):667-671 (2009).
Gahete et al., Role of ghrelin system in neuroprotection and cognitive functions: implications in Alzheimer's disease, Peptides, 32(11):2225-2228 (2011).
Tschop et al., Ghrelin induces adiposity in rodents, Nature, 407:908-913 (2000).
Bednarek et al., Structure-Function Studies on the New Growth Hormone-Releasing Peptide, Ghrelin: Minimal Sequence of Ghrelin Necessary for Activation of Growth Hormone Secretagogue Receptor 1, J. Med. Chem., 43:4370-4376 (2000).
Diano et al., Ghrelin controls hippocampal spine synapse density and memory performance, Naure Neuroscience, 9(3):381-388 (2006).
Druce et al., Ghrelin increases food intake in obese as well as lean subjects, International Journal of Obesity, 1-7 (2005).
Gauna et al., Administration of Acylated Ghrelin Reduces Insulin Sensitivity, Whereas the Combination of Acylated Plus Unacylated Ghrelin Strongly Improves Insulin Sensitivity. The Journal of Clinical Endocrinology & Metabolism, 89(10):5035-5042 (2004).
Hanada et al., Anti-cachectic effect of ghrelin in nude mice bearing human melanoma cells, Biochemical and Biophysical Research Communications, 301:275-279 (2003).
Hosoda et al., Ghrelin and Des-acyl Ghrelin: Two Major Forms of Rat Ghrelin Peptide in Gastrointestinal Tissue, Biochemical and Biophysical Research Communications, 279:909-913 (2000).
Kojima et al., Ghrelin: Structure and Function, Physiol Rev., 85:495-522 (2005).
Moon et al., Ghrelin ameliorates cognitive dysfunction and neurodegeneration in intrahippocampal amyloid-B1-42 oligomer-injected mice, Journal of Alzheimer's Disease, 23(2011):147-159 (2010).
Nagaya et al., Treatment of cachexia with ghrelin in patients with COPD, CHEST, 128(3):1187-1193 (2005).
Nagaya et al., Effects of Ghrelin Administration on Left Ventricular Function, Exercise Capacity, and Muscle Wasting in Patients With Chronic Heart Failure, Circulation, 3674-3679 (2004).

(Continued)

*Primary Examiner* — John D Ulm
(74) *Attorney, Agent, or Firm* — Browdy and Neimark, PLLC

(57) ABSTRACT

The present disclosure relates, in one aspect, to use of ghrelin splice variant or an analogue thereat: or a ghrelin splice variant-like compound for the preparation of a medicament for one or more of: treatment and/or prevention of neuronal damage and/or neurodegeneration and, prophylaxis or treatment of neuronal damage and/or neurodegenerative disease, Parkinson's disease, Alzheimer's disease, depression stimulation of neuronal activity. A further aspect relates to a number of new ghrelin splice variant like compounds and uses thereof, as well as to pharmaceutical compositions and medical packaging comprising the new ghrelin splice variant-like compounds.

10 Claims, 6 Drawing Sheets

Specification includes a Sequence Listing.

(56) References Cited

OTHER PUBLICATIONS

Neary et al., Ghrelin Increases Energy Intake in Cancer Patients with Impaired Appetite: Acute, Randomized, Placebo-Controlled Trial, The Journal of Clinical Endocrinology & Metabolism, 89(6):2832-2836 (2004).

Pemberton et al, C-terminal pro-ghrelin peptides are present in the human circulation, Biochemical and Biophysical Research Communications, 310:567-573 (2003).

Wren et al., Ghrelin Causes Hyperphagia and Obesity in Rats, Diabetes, 50:2540-2547 (2001).

Wren et al., Ghrelin enhances appetite and increases food intake in humans, The Journal of Clinical Endocrinology & Metabolism, 86(12):5992-5995 (2001).

Kern et al., Apo-ghrelin receptor forms heteromers with DRD2 in hypothalamic neurons and is essential for anorexigenic effects of DRD2 agonism, Neuron., 73(2)L317-332 (2012).

Strasser, Clinical Application of Ghrelin, Current Pharmaceutical Design, 18:4800-4812 (2012).

Carlini et al., Acute ghrelin administration reverses depressive-like behavior induced by bilateral olfactory bulbectomy in mice, Peptides, 35:160-165 (2012).

Zhang et al., Obestatin, a Peptide Encoded by the Ghrelin Gene, Opposes Ghrelin's Effects on Food Intake, Science, 310, 996 (2005).

Uc et al., Predictors of Weight Loss in Parkinson's Disease, Movement Disorder Society, 21(7):930-936 (2006).

Neufelf et al., Vascular endothelial growth factor (VEGF) and its receptors, FASEB, 13:9-22 (1999).

Chen et al., Weight Loss in Parkinson's Disease, Ann Neurol, 53:676-679 (2003).

Kluge et al., Effects of ghrelin on psychopathology, sleep and secretion of cortisol and growth hormone in patients with major depression, Journal of Psychiatric Research, 45:421-426 (2011).

\* cited by examiner

SEQUENCE LISTING

```
<160> NUMBER OF SEQ ID NOS: 8

<210> SEQ ID NO 1
<211> LENGTH: 94
<212> TYPE: PRT
<213> ORGANISM: Homo sapiens

<400> SEQUENCE: 1

Gly Ser Ser Phe Leu Ser Pro Glu His Gln Arg Val Gln Val Arg Pro
1               5                   10                  15

Pro His Lys Ala Pro His Val Val Pro Ala Leu Pro Leu Ser Asn Gln
            20                  25                  30

Leu Cys Asp Leu Glu Gln Gln Arg His Leu Trp Ala Ser Val Phe Ser
        35                  40                  45

Gln Ser Thr Lys Asp Ser Gly Ser Asp Leu Thr Val Ser Gly Arg Thr
    50                  55                  60

Trp Gly Leu Arg Val Leu Asn Gln Leu Phe Pro Pro Ser Ser Arg Glu
65                  70                  75                  80

Arg Ser Arg Arg Ser His Gln Pro Ser Cys Ser Pro Glu Leu
                85                  90
```

```
<210> SEQ ID NO 2
<211> LENGTH: 22
<212> TYPE: PRT
<213> ORGANISM: Homo sapiens

<400> SEQUENCE: 2

Gly Ser Ser Phe Leu Ser Pro Glu His Gln Arg Val Gln Val Arg Pro
1               5                   10                  15

Pro His Lys Ala Pro His
            20

<210> SEQ ID NO 3
<211> LENGTH: 24
<212> TYPE: PRT
<213> ORGANISM: Homo sapiens

<400> SEQUENCE: 3

Gly Ser Ser Phe Leu Ser Pro Glu His Gln Arg Val Gln Val Arg Pro
1               5                   10                  15

Pro His Lys Ala Pro His Val Val
            20

<210> SEQ ID NO 4
<211> LENGTH: 24
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Dpr

<400> SEQUENCE: 4

Gly Ser Xaa Phe Leu Ser Pro Glu His Gln Arg Val Gln Val Arg Pro
1               5                   10                  15

Pro His Lys Ala Pro His Val Val
            20

<210> SEQ ID NO 5
<211> LENGTH: 29
<212> TYPE: PRT
<213> ORGANISM: Homo sapiens

<400> SEQUENCE: 5

Gly Ser Ser Phe Leu Ser Pro Glu His Gln Arg Val Gln Val Arg Pro
1               5                   10                  15

Pro His Lys Ala Pro His Val Val Pro Ala Leu Pro Leu
            20                  25

<210> SEQ ID NO 6
<211> LENGTH: 91
<212> TYPE: PRT
<213> ORGANISM: Homo sapiens

<400> SEQUENCE: 6

Phe Leu Ser Pro Glu His Gln Arg Val Gln Val Arg Pro Pro His Lys
1               5                   10                  15

Ala Pro His Val Val Pro Ala Leu Pro Leu Ser Asn Gln Leu Cys Asp
            20                  25                  30

Leu Glu Gln Gln Arg His Leu Trp Ala Ser Val Phe Ser Gln Ser Thr
        35                  40                  45

Lys Asp Ser Gly Ser Asp Leu Thr Val Ser Gly Arg Thr Trp Gly Leu
    50                  55                  60
```

Arg Val Leu Asn Gln Leu Phe Pro Pro Ser Ser Arg Glu Arg Ser Arg
65                  70                  75                  80

Arg Ser His Gln Pro Ser Cys Ser Pro Glu Leu
                85                  90

<210> SEQ ID NO 7
<211> LENGTH: 181
<212> TYPE: PRT
<213> ORGANISM: Mus musculus

<400> SEQUENCE: 7

Gly Ser Ser Phe Leu Ser Pro Glu His Gln Lys Ala Gln Val Ser Gln
1               5                   10                  15

Ser Val Ser Leu Ser Pro His Ile Tyr Pro Asp Leu Cys Val Cys Val
                20                  25                  30

Arg Glu Arg Glu Arg Glu Pro Ser Phe Pro Phe Gln Gln Arg Lys Glu
            35                  40                  45

Ser Lys Lys Pro Pro Ala Lys Leu Gln Pro Arg Ala Leu Glu Gly Trp
50                  55                  60

Leu His Pro Glu Asp Arg Gly Gln Ala Glu Thr Glu Glu Glu Leu
65                  70                  75                  80

Glu Ile Arg Val Cys Thr Gln Ala Pro Ala Cys Ser Tyr Asn Ser Lys
                85                  90                  95

Gly Val Gly Val Trp Arg Val Ser His Met Leu Ala Phe Gln Ala Thr
            100                 105                 110

Gln Gly Leu Glu Ser Ser Thr Asn Ser Ser Thr Arg Gly Ser Glu Ser
            115                 120                 125

Pro Ser Gln Glu Val Thr Val Ser Arg Val Ala Arg Glu Gln Gln Thr
130                 135                 140

Cys Ala Gln Lys Thr Lys Gln Ile Glu Gly Ser Gln Glu Pro Gly Ser
145                 150                 155                 160

Thr Asp Gly Tyr Arg Asn Arg Arg Lys Pro Cys Leu Ser Gln Asp Leu
                165                 170                 175

Ser Gly Leu Pro Trp
            180

<210> SEQ ID NO 8
<211> LENGTH: 90
<212> TYPE: PRT
<213> ORGANISM: Rattus norvegicus

<400> SEQUENCE: 8

Gly Ser Ser Phe Leu Ser Pro Glu His Gln Lys Ala Gln Val Ser Leu
1               5                   10                  15

Ser Pro Gln Val Pro His Leu Ser Trp Ser Val Val Cys Ser Phe Pro
                20                  25                  30

Phe Gln Gln Arg Lys Glu Ser Lys Lys Pro Pro Ala Lys Leu Gln Pro
            35                  40                  45

Arg Ala Leu Glu Gly Trp Leu His Pro Glu Asp Arg Gly Gln Ala Glu
50                  55                  60

Glu Ala Glu Glu Glu Leu Glu Ile Arg Val Gly Pro Arg Ala Pro Ala
65                  70                  75                  80

Tyr Ser Cys Asn Ser Lys Gly Phe Gly Val
                85                  90

GHRELIN SPLICE VARIANT FOR TREATING NEURONAL DAMAGE, NEURODEGENERATIVE DISEASE, PARKINSONS DISEASE, ALZHEIMERS DISEASE, AND/OR DEPRESSION

FIELD OF INVENTION

The present disclosure relates to compounds for treating or preventing neurodegeneration and/or Parkinson's disease and/or Alzheimer's disease and/or depression and conditions related thereto.

BACKGROUND OF INVENTION

Alzheimer's disease (AD) and Parkinson's disease (PD) are the two most common neurodegenerative disorders. Parkinson's disease (PD) is characterized by the progressive degeneration of dopamine (DA) neurons projecting from the substantia nigra pars compacta (SNpc) to the dorsal striatum. The resulting loss of dopamine in the striatum leads to debilitating motor dysfunction, including rigidity, resting tremor, postural instability, and bradykinesia. Familial or genetic causes of PD only account for 10% of all cases, whereas 90% are considered sporadic and may manifest as a result of a variety of factors. Currently available therapies for Parkinson's disease (PD) provide relief of motor symptoms, but fall short of exhibiting the neuroprotective effect required to prevent progressive degeneration of dopamine (DA) neurons. Furthermore, no therapies simultaneously target the multiple, debilitating, non-motor symptoms of PD.

Alzheimer's disease (AD) is a multifactorial progressive neurodegenerative disorder characterized by loss of memory and cognitive deficits, strongly influenced by the metabolic status, in which the impairment of neuropeptides/neurotransmitters systems has been previously observed. Currently available therapies for Alzheimer's disease (AD) have shown limited efficacy, with no true cure to this day being present. Recent work, both clinical and experimental, indicates that many neurodegenerative disorders often display a coexisting metabolic dysfunction which may exacerbate neurological symptoms. It stands to reason therefore that metabolic pathways may themselves contain promising therapeutic targets for major neurodegenerative diseases.

Ghrelin is a bioactive peptide that induces food intake, body weight gain, and adiposity in rodents (Tschop M. et al., Nature 407:908-13 (2000); Wren A. M. et al., Diabetes 50:2540-47 (2001)). Acute administration of ghrelin induces food intake in healthy men and women (Wren A. M. et al., J. Endocrinol. Metab. 86:5992-95 (2001): Druce M. R. et al., Int. J. Obes. Relat. Metab. Disord. 29:1130-36 (2005)) as well as in cancer patients with anorexia (Neary N. M. et al., J. Clin. Endocrinol. Metab. 89:2832-36 (2004)). Repeated administration of ghrelin increases lean body mass, body weight and food intake in cachectic patients with Chronic Obstructive Pulmonary Disease (COPD) (Nagaya N. et al., Chest 128:1187-93 (2005)) and improved muscle wasting in patients with chronic heart failure (Nagaya N. et al., Circulation 110:3674-79 (2004)). A similar effect was also shown in a mouse model (Hanada T. et al., Biochem. Biophys. Res. Commun. 301:275-79 (2003)).

Ghrelin has been associated with the progression of obesity and metabolic syndrome, but has been also linked to neuromodulation, neuroprotection and memory and learning processes. In addition, ghrelin system also acts in an autocrine/paracrine fashion where the majority of its components ghrelin variants, acylation enzyme (GOAT) and receptors (GHS-Rs)] are expressed in the different regions of central nervous system. Gahete et al. analyzed the mRNA expression of the ghrelin system in three different regions of the temporal gyros (inferior, medial and superior) of control and AD human brains, since the temporal lobe is considered as one of the most important cortical structures in memory and cognition, and is one of the most affected regions in AD (Gahete et al., Peptides 32: 2225-2228 (2011)). This report showed, for the first time, that AD patients have a reduction in local brain ghrelin production, as compared with age-matched controls. In addition, they analyzed the expression of a newly described In1-ghrelin splice variant (In1-ghrelin is identical to applicants SEQ ID 32 from U.S. Pat. No. 7,176,292), which could also be acylated by the ghrelin-O-acyltransferase (GOAT) enzyme. Results revealed that, similar to ghrelin, In1-ghrelin variant (In1-ghrelin is applicants SEQ ID 32 from U.S. Pat. No. 7,176,292) is also expressed in the temporal lobe, and is down-regulated in AD, thereby showing, together with ghrelin, a region-dependent alteration with AD. Consistent with a similar distribution between ghrelin and GOAT in other tissues, GOAT was also expressed in the temporal lobe of the brain and was impaired in AD, suggesting that a functional autocrine and/or paracrine pathway might be in place within the temporal lobe, and that changes in locally produced acylated/non-acylated ghrelin and In1-ghrelin variant may be of (paths)-physiologically relevance.

The first evidence showing a direct effect of ghrelin on AD-like alterations was reported in a mouse model widely used to examine the pathophysiology of early defects seen in AD. The senescence-accelerated mouse prone8 or SAMP8 mice develop early abnormalities in learning and memory related to abnormalities in septa-hippocampal function, which are due to overproduction of β-amyloid. In this mouse model, ghrelin was able to improve retention of T-maze foot shock avoidance in 12 and 14 month-old mice, compared to their controls (Diano et al. Nat Neurosci. 9:381-8 (2006)). More recently, a different mouse model has been used to analyze in more detail the role that ghrelin plays in AD-related endpoints. This model was generated by intrahippocampal injection of oligomeric forms of the Aβ peptide (AβO), which have been directly related with AD-associated damage (Moon et al. J. Alzheimers Dis.; 23:1.47-59 (2011)). Results of this study revealed that systemic injection of ghrelin rescues memory deficits observed following intra-hippocampal AβO injection, using two independent behavioral paradigms (Y-maze and passive avoidance tasks). In addition, the AD-associated neuropathological abnormalities observed in these AβO mice were also attenuated by ghrelin. Indeed, ghrelin inhibited the reactive microgliosis originated by AβO, thus preventing the inflammatory response. Ghrelin also prevented AβO-induced neuronal cell loss in the dentate gyrus and increased the density of hippocampal synaptic and cholinergic nerve fibers. Collectively, these data show that systemic injection of ghrelin rescue cognitive impairments induced by AβO, possibly through inhibition of both, microgliosis and impairment of neuronal integrity.

Recent data (Andrews et al. The Journal of Neuroscience 29(45):14057-14065 (2009)) demonstrate that ghrelin administration decreases substantia nigra pars compacta DA, cell loss and limits striatal DA loss in a PD mouse model. Ghrelin has also been shown to defend against depression (Lutter et al. Nature Neuroscience 11(7):752-3 (2008)) and to stimulate appetite (Tschop M. et al., Nature 407:908-13 (2000); Wren A. M. et al., Diabetes 50:2540-47 (2001)) in animal models, suggesting additional benefit to these distressing non-motor symptoms of PD (Uc et al. Movement Disorders 21(7):930-6 (2006); Chen et al. Annual Neurology 53(5):676-9 (2003); Delinkanaki-Skaribas et al. Movement Disorders 15; 24(5):667-71 (2009)). It was also shown that subjects at putative preclinical (iRBD) and clinical stages of PD suffer from an impaired ghrelin excretion. Lately it was shown that the GHSR1 and DRD2 receptors form heteromers in hypothalamic neurons and that you can inhibit dopamine signaling using GHSR1 antagonists (Kern A. et al., Neuron 73:317-332 (2012)). From the studies conducted, ghrelin has an acute effect on the firing rate of SNpc DA neurons, which enhances dopamine availability during the course of degeneration and lowers the loss of dopamine levels in the dorsal striatum. In addition, ghrelin-induced enhancement of UCP2-dependent mitochondrial respiration and proliferation provides a bioenergetic status that makes these neurons more resistant to cellular stress. UCP2 is a mitochondrial protein known to protect SNpc DA cells from MPTP intoxication5. Ghrelin also regulates UCP2 mRNA in the brain, consistent with the role of UCP2 as a component of ghrelin-induced neuroprotection. Ghrelin-/- and ghsr-/- mice were more susceptible to DA cell loss in the SNpc and DA loss in the striatum after MPTP than their wt littermates. This suggests that any factor leading to reduced ghrelin production or secretion, whether genetic or environmental, may predispose individuals to nigrostriatal dopaminergic dysfunction. Taken together, these data provide a strong biological rationale for ghrelin peptide family as a novel class of neurodegenerative diseases therapeutics that promotes neuroprotection and relieves non-motor symptoms.

The GHRL (ghrelin) gene encodes a variety of products resulting from alternatively spliced transcripts, various types of cleavage of the prepropeptide, and various post-translational modifications (Kojima M. & Kangawa M., Physiol. Rev. 85:495-522 (2005); Zhang J. V. et al., Science 310: 996-99 (2005)). In addition, different degradation products are produced by various tissues (De Vriese C. et al., Endocrinology 145:4997-5005 (2004)). Some of these GHRL products are described herein.

Ghrelin is a 28 amino acid peptide bearing an n-octanoyl side chain on the third serine, resulting from the cleavage of signal and propeptide from the 117 amino acid preproghrelin and an acylation event. The acylated N-terminus of ghrelin is essential for the endocrine functions (Kojima M. et al., Nature 402:656-60 (1999); Bednarek M. A. et al., J. Med. Chem. 43:4370-76 (2000)). Des-acyl ghrelin, which lacks the endocrine functions, was shown to have an antagonistic effect to that of ghrelin on glucose output in vitro (Gauna C. et al., J. Clin. Endocrinol. Metab. 89:5035-42 (2004)). An alternatively-spliced ghrelin mRNA encodes a 116 amino acid prepropeptide that is further processed to a Des-Gln14-ghrelin and a 27 amino acid processed peptide (Hosoda H. et al., J Biol. Chem. 275:21995-22000 (2000)). Another peptide, Obestatin, is cleaved from the preproghrelin and has no sequence overlap with processed ghrelin peptide. This peptide was shown to have some antagonistic effect to acylated ghrelin, inhibiting food intake and body weight gain (Zhang J. V. et al., Science 310:996-99 (2005)). Yet another peptide, the 66 amino acid C-terminus of the preproghrelin, may also be functional (Pemberton C. et al., Biochem. Biophys. Res. Comm. 310:567-73 (2003)). A variety of isoforms, including isoforms encoded by different splice variants, are known for other proteins, e.g. for vascular endothelial growth factor (VEGF), where different isoforms share roles as angiogenesis, while differing in some other characteristics, such as binding affinity (Neufeld G. et al., FASEB J. 13:9-22 1999). Thus, the variety of products of the GHRL gene may reflect a similarly complex control of the endocrine and paracrine action of the ghrelin isoforms.

Previously, administration of ghrelin by continuous infusions of 5 pmol/kg/min doses for 270 minutes was shown to increase food intake in healthy humans (Wren A. M. et al., J. Clin. Endocrinol. Metab. 86:5992-95 (2001)). It was also shown that infusion of ghrelin for 90 minutes could increase food intake by 30% in cancer cachexia patients (Abstract P09, Digestive Hormones, Appetite and Energy Balance, Baylis and Starling meeting, London, June 2003). Recently, it was shown that subcutaneous injection of 3.6 nmol/kg acylated ghrelin prior to a meal, thereby ensuring a close mimic of the natural pre-meal situation, increased energy intake by 27%. Ghrelin also appeared to enhance the perceived palatability of the food offered (Druce M. R. et al., Int. J. Obes. Relat. Metab. Disord. 29:1130-36 (2005)).

These studies demonstrate that parenteral administration of ghrelin can increase appetite in both normal subjects and in patients with loss of appetite. Furthermore, Applicant has found that it is possible to obtain a significant effect of body weight gain and a significant increase in food consumption with a novel ghrelin splice variant (see co-owned, published U.S. Pat. No. 7,981,860 and/or U.S. Pat. No. 7,763,707, incorporated herein by reference) when administered to a subject, in particular when administered subcutaneously prior to a meal, thereby ensuring a close mimic of the natural pre-meal situation. Applicant's novel ghrelin splice variant effect of weight gain is mainly on lean mass mass while ghrelin's effect on weight gain is mainly on fat mass.

In addition applicant has found that it is possible to decrease substantia nigra pars compacta DA cell loss and limits striatal DA loss with a novel ghrelin splice variant (see co-owned, published U.S. Pat. No. 7,981,860 and/or U.S. Pat. No. 7,763,707, incorporated herein by reference) when administered to a subject in a PD animal model.

SUMMARY OF THE INVENTION

One aspect is a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1.

Another aspect is a pharmaceutical composition comprising the ghrelin splice variant like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1.

A further aspect is a method of treating Parkinson's Disease comprising administering to a mammal in need thereof a pharmaceutically acceptable amount of (a) ghrelin splice variant; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

An additional aspect is a method for preventing Parkinson's Disease comprising administering to a mammal in need thereof a pharmaceutically acceptable amount of (a) ghrelin splice variant; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; in is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

A further aspect is a method of treating Alzheimer's Disease comprising administering to a mammal in need thereof a pharmaceutically acceptable amount of (a) ghrelin splice variant; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

An additional aspect is a method for preventing Alzheimer's Disease comprising administering to a mammal in need thereof a pharmaceutically acceptable amount of (a) ghrelin splice variant; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

A further aspect is a method for the stimulation of neuronal activity comprising administering to a mammal in need thereof a pharmaceutically acceptable amount of (a) ghrelin splice variant; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

Another aspect is a method for treating depression comprising administering to a mammal in need thereof a pharmaceutically acceptable amount of (a) ghrelin splice variant; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; in is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

A further aspect is a method for preventing depression comprising administering to a mammal in need thereof a pharmaceutically acceptable amount of (a) ghrelin splice variant; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

Another aspect is a method for treating neuronal degeneration comprising administering to a mammal in need thereof a pharmaceutically acceptable amount of (a) ghrelin splice variant; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1(X1)m-(X2)-(X3)n-Z2 is 15-94 amino acids in length and has at least 80% homology to SEQ ID NO:1; or (c) a mixture thereof.

A further aspect is a method for preventing neuronal degeneration comprising administering to a mammal in need thereof a pharmaceutically acceptable amount of (a) ghrelin splice variant; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (c) a mixture thereof.

An additional aspect is a method of treating Parkinson's Disease and/or depression and/or neuronal degeneration comprising administering to a mammal in need thereof a pharmaceutically acceptable amount of a secretagogue comprising (a) ghrelin splice variant; (b) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (e) a mixture thereof; wherein treatment is selected from the group consisting of prophylaxis or treatment of Parkinson's disease, prophylaxis or treatment of Alzheimer's disease, prophylaxis or treatment of depression, stimulation of neuronal activity, stimulation of neuronal regeneration, stimulation of appetite, stimulation of weight gain, increasing body fat mass, increasing lean body mass, or a combination thereof.

A further aspect is a kit for administering ghrelin splice variant or a ghrelin splice variant-like compound comprising (a) a dosage form comprising a pharmaceutically acceptable amount of (1) ghrelin splice variant; (2) a ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic, amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% homology to SEQ ID NO:1; or (3) a mixture thereof; and (b) optionally, instructions for administering (a).

Another aspect is for a method of producing a ghrelin splice variant-like compound, said method comprising: (a) providing a cDNA comprising a polynucleotide sequence encoding a ghrelin splice variant-like compound as described above; (b) inserting said cDNA in an expression vector such that the cDNA is operably linked to a promoter; (c) introducing said expression vector into a host cell whereby said host cell produces said ghrelin splice variant-like compound; and (d) optionally recovering the ghrelin splice variant-like compound produced in step (c).

An additional aspect is for use of an isolated ghrelin splice variant-like compound having the formula Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length, has at least 95% homology to SEQ ID NO:1 in the manufacture of a medicament for the induction of neuron function, protection of neuron function, alteration neuron function, or a combination thereof.

Other objects and advantages will become apparent to those skilled in the art upon reference to the detailed description that hereinafter follows.

BRIEF DESCRIPTION OF THE SEQUENCES

SEQ ID NO:1 represents human prepro ghrelin splice variant after the signaling sequence.

SEQ ID NO:2 represents 22 amino acid human ghrelin splice variant.

SEQ ID NO:3 represents 24 amino acid human ghrelin splice variant.

SEQ ID NO:4 represents 24 amino acid modified human ghrelin splice variant.

SEQ ID NO:5 represents 29 amino acid human ghrelin splice variant.

SEQ ID NO:6 represents a fragment of full-length human glitch splice variant.

SEQ ID NO:7 represents mouse prepro ghrelin splice variant after the signaling sequence.

SEQ ID NO:8 represents rat prepro ghrelin splice variant after the signaling sequence.

BRIEF DESCRIPTION OF THE FIGURES

For the purpose of illustrating the invention, there are depicted in the drawings certain embodiments of the invention. However, the invention is not limited to the precise arrangements and instrumentalities of the embodiments depicted in the drawings.

In FIG. 1 it is clearly shown that the toxicity of H2O2 leads to the survival of only 50% of the cells. It is also clear that treatment with Ghrelin splice variant alone or in combination with Ghrelin exerts an effective protective action against the damages produced by H2O2. Specifically H2O2 Ghrelin splice variant & H2O2+Ghrelin & H2O2+Ghrelin+Ghrelin splice variant treatments are statistically significant in terms of cell viability compared to the negative control H2O2. Furthermore, the efficacy of Ghrelin splice variant seems to be greater than that of Ghrelin.

DETAILED DESCRIPTION OF THE INVENTION

Figure 1:
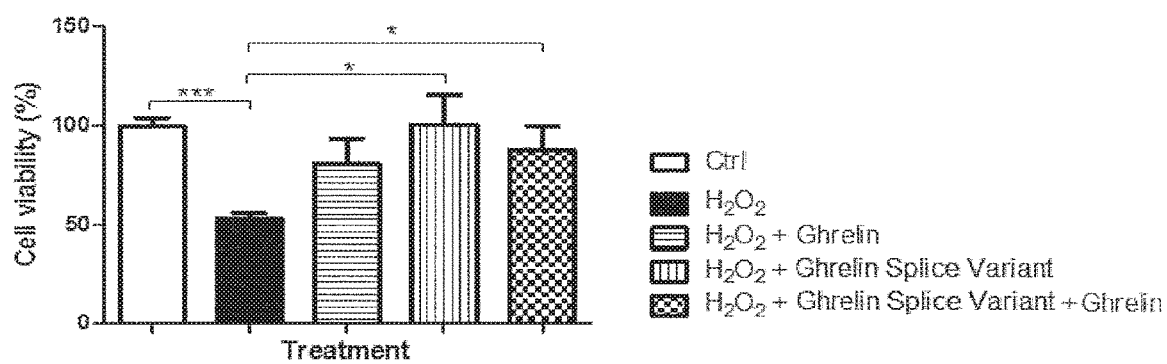
FIG. 1.

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

In the context of this disclosure, a number of terms shall be utilized.

"Affinity" as used herein means the strength of binding between receptors and their ligands, for example between an antibody and its antigen.

"Amino acid residue" as used herein means an amino acid formed upon chemical digestion (hydrolysis) of a polypeptide at its peptide linkages. The amino acid residues described herein are preferably in the "L" isomeric form. However, the amino acid encompasses every amino acid such as L-amino acid, D-amino acid, alpha-amino acid, beta-amino acid, gamma-amino acid, natural amino acid and synthetic amino acid or the like as long as the desired functional property is retained by the polypeptide. $NH_2$ refers to the free amino group present at the amino terminus of a polypeptide. COOH refers to the free carboxy group present at the carboxy terminus of a polypeptide. Standard polypeptide abbreviations for amino acid residues are shown in Table 1.

TABLE 1

| 1-Letter Code | 3-Letter Code | Amino Acid |
| --- | --- | --- |
| A | Ala | Alanine |
| B | Asx, Asn, and/or Asp | Aspartic Acid and/or Asparagine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| X | Xaa | Unknown or Other |
| Y | Tyr | Tyrosine |

TABLE 1-continued

| 1-Letter Code | 3-Letter Code | Amino Acid |
|---|---|---|
| Z | Glx, Gln, and/or Glu | Glutamic Acid and/or glutamine |
| — | Dpr | 2,3-diaminopropionic acid |

It should be noted that all amino acid residue sequences represented herein by formula have a left-to-right orientation in the conventional direction of amino terminus to carboxy terminus. In addition, the phrase "amino acid residue" is broadly defined to include the amino acids listed in the Table 1 and modified and non-naturally occurring amino acids. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

"Parkinson's disease" as used herein means a slowly progressive neurologic disease characterized by a fixed inexpressive face, a tremor at rest, slowing of voluntary movements, a gait with short accelerating steps, peculiar posture and muscle weakness, caused by degeneration of an area of the brain called the basal ganglia, and by low production of the neurotransmitter dopamine.

"Parkinson's disease specific assessments" as used herein means tests used to assess the severity of Parkinson's disease in a mammal. For example: Parts I, II, and III of the revised Movement Disorders Society Unified Parkinson Disease Rating Scale (MDS-UPDRS) (Goetz et al. Mov Disord 15; 23(15):2129-70 (2008)) and/or Geriatric Depression Scale (GDS) (Yesavage et al. J Psychiatr Res 17(1): 37-49 (1982)) and/or The Montreal Cognitive Assessment (MoCA) (Nasreddine et al. J Am Geriatr Soc; 53(4):695-9 (2005))

"Activating a neuron" as used herein refers to increasing the action potential frequency (i.e., firing rate) above baseline. Baseline frequency is the frequency in the absence of a ghrelin or ghrelin mimetic. A dopamine neuron releases dopamine when it is activated.

"Alzheimer's disease" as used herein means a multifactorial progressive neurodegenerative disorder characterized by loss of memory and cognitive deficits, strongly influenced by the metabolic status, in which the impairment of neuropeptides/neurotransmitters systems has been previously observed. Alzheimer's disease is the most common form of both senile and presenile dementia in the world and is recognized clinically as relentlessly progressive dementia that presents with increasing loss of memory, intellectual function and disturbances in speech (Merritt, 1979, A Textbook of Neurology, 6th edition, pp. 484-489 Lea & Febiger, Philadelphia). The disease itself usually has a slow and insidious progress that affects both sexes equally, worldwide. It begins with mildly inappropriate behavior, uncritical statements, irritability, a tendency towards grandiosity, euphoria and deteriorating performance at work; it progresses through deterioration in operational judgement, loss of insight, depression and loss of recent memory; it ends in severe disorientation and confusion, apraxia of gait, generalized rigidity and incontinence (Gilroy & Meyer, 1979, Medical Neurology, pp. 175-179 MacMillan Publishing Co.). Alzheimer's disease afflicts an estimated 4 million human beings in the United States alone at a cost of 35 billion dollars a year (Hay & Ernst, 1987, Am. J. Public Health, 77:1169-1175). It is found in 10% of the population over the age of 65 and 47% of the population over the age of 85 (Evans et al., 1989, JAMA, 262:2551-2556). In addition, the disease is found at much lower levels in the younger age groups, usually beginning at about 30 years of age and even rarely in late childhood (Adams & Victor, 1977, Principles of Neurology, pp. 401-407). The etiology of Alzheimer's disease is unknown.

"Body Mass Index" or "BMI" is a measure of an individual's height to weight ratio. BMI is determined by calculating weight in kilograms divided by the square of height in meters. The BMI "normal" range is 18.5-25.

"Body fat mass" can be measured, e.g., by the fat fold technique. In the fat fold technique, a pincer-type caliper is used to measure subcutaneous fat by determining skin fold thickness at representative sites on the body. These skin fold measurements are then used to compute body fat by either adding the scores from the various measurements, and using this value as an indication of the relative degree of fatness among individuals, or by using the measurements in mathematical equations that have been developed to predict percent body fat (Fogelholm M. & van Marken Lichtenbelt W., Eur. J. Clin. Nutr. 51:495-503 (1997)).

"Concentration equivalent" as used herein means an equivalent dosage of a ghrelin splice variant-like compound having in vitro and/or in vivo the same response as evaluated from a dosage-response curve of the ghrelin splice variant.

"Dissociation constant" or "Kd" is a measure describing the strength of binding, affinity or avidity) between receptors and their ligands, for example an antibody and its antigen. The smaller the Kd, the stronger the binding.

A "fusion polypeptide" is a polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

"Human ghrelin" as used herein is a polypeptide having the amino acid sequence as set forth in GenBank® Accession No. NP_057446 or Swiss-Prot Identifier GHRL_HUMAN. Human ghrelin preprotein has 117 amino acids. This preprotein undergoes the following post-translational processing. The signal peptide (amino acids 1-23) is removed and the remaining 94 amino acids are cleaved by a protease to provide a mature 28 amino acid ghrelin (amino acids 24-51) or a mature 27 amino acid ghrelin (amino acids 24-50) and a mature 23 amino acid obestatin (amino acids 76-98). The 27 or 28 amino acid mature ghrelin peptides can be further modified at the serine at position 26 in the preprotein by either an O-octanoyl group or an O-decanoyl group. The obestatin mature peptide can be further modified at the lysine at position 98 of the preprotein by an amide group. An additional ghrelin preprotein is known, which lacks the glutamine at position 37 of the preprotein.

"Ghrelin splice variant" is a polypeptide having the amino acid sequence as set forth in SEQ ID NO:1 or any peptide of 15 amino acids or more from SEQ ID NO:1 with or without post translational modification, or any SEQ ID NO:1 homologs as set forth in SEQ ID NO:7 or SEQ ID NO:8, and/or any peptide of 15 amino acids or more from SEQ ID NO:7 or SEQ ID NO:8 with or without post translational modification.

"Ghrelin splice variant-like compound" as used herein refers to any compound which mimics the function of ghrelin splice variant, in particular human ghrelin splice variant, particularly in terms of the ghrelin splice variant functions leading to the desired therapeutic effects described herein, such as stimulation of appetite and/or treatment and/or prophylaxis of neurodegeneration and is defined by the Formula I: Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% (or, in alternative embodiments, 85%, 90%, 93%, 95%, 97%, 98%, 99%, 100%) homology to SEQ. ID NO:1. In a preferred embodiment, the ghrelin splice variant-like compound is 22-29 amino acids in length.

"Immunologically distinct" refers to the ability to distinguish between two polypeptides on the ability of an antibody to specifically bind one of the polypeptides and not specifically bind the other polypeptide.

An "individual" is an animal or human susceptible to a condition, in particular a cachectic condition as defined herein. In preferred embodiments, the individual is a mammal, including human, and non-human mammals such as dogs, cats, pigs, cows, sheep, goats, horses, rats, and mice. In the most preferred embodiment, the individual is a human.

"Isolated" is used to describe the various ghrelin splice variant-like compounds, i.e. polypeptides and nucleotides disclosed herein, that have been identified and separated and/or recovered from a component of its natural environment. Contaminant components of a natural environment are materials that would typically interfere with diagnostic or therapeutic uses for the polypeptide, and may include enzymes, hormones, and other proteinaceous or non-proteinaceous solutes. In preferred embodiments, the ghrelin splice variant-like compounds will be purified.

"Modified amino acid" as used herein is an amino acid wherein an arbitrary group thereof is chemically modified.

"Non-standard amino acid" as used herein is an amino acid that does not belong to the standard 20 amino acids. Non-standard amino acids are usually formed through chemical modifications to standard amino acids. They can also be formed naturally as an intermediate component of a metabolic pathway or by microorganisms and/or plants.

"Monoclonal Antibody", in its various grammatical forms, refers to a population of antibody molecules that contains only one species of antibody combining site capable of immunoreacting with a particular antigen.

A "non-acylated ghrelin splice variant-like compound" is a ghrelin splice variant-like compound, as defined herein, which does not contain an acyl group attached to any of its constituent amino acids.

"Palliative treatment" is a treatment which relieves or sooths the symptoms of a disease or disorder but without a curing effect.

"Polyclonal antibodies" are a mixture of antibody molecules recognizing a specific given antigen; hence, polyclonal antibodies may recognize different epitopes within said antigen.

"Polypeptide" refers to a molecule comprising amino acid residues which do not contain linkages other than amide linkages between adjacent amino acid residues.

"Processed ghrelin" means the 27 or 28 amino acid residue, acylated ghrelin (the post-translational product of cleavage and acylation of 116 and 117 amino acid residues long preproghrelin, respectively (e.g., SWISS-PROT Q9UBU3 GHRL_HUMAN)).

A "receptor" is a molecule, such as a protein, glycoprotein and the like, that can specifically (non-randomly) bind to another molecule.

A "secretagogue" is a substance stimulating growth hormone release, such as ghrelin or a ghrelin-like compound. A secretagogue according to the present disclosure may for example be selected from L-692-429 and L-692-585 (benzoelactam compounds; available from Merck &; Co, Inc., Whitehouse Station, N.J.), MK677 (spiroindaner; available from Merck) G-7203, G-7039, G-7502 (isonipecotic acid peptidomimetic; available from Genentech, Inc., South San Francisco, Calif.), NN703 (Novo Nordisk Inc., Princeton, N.J.), or ipamorelin. In particular, the secretagogue is a ghrelin splice variant-like compound, including a 29 amino acid human ghrelin splice variant, a 24 amino acid human ghrelin splice variant, or a 22 amino acid human ghrelin splice variant (e.g., SEQ ID NO:2, SEQ ID NO:3, SEQ ID NO:4, or SEQ ID NO:5). The growth hormone secretagogue may in one embodiment be non-acylated, for instance a non-acylated form of ghrelin splice variant or a non-acylated ghrelin splice variant-like compound.

A "surfactant molecule" is a molecule comprising a hydrophobic part and a hydrophilic part; i.e. a molecule capable of being present in the interphase between a lipophilic phase and a hydrophilic phase.

Indications

The present disclosure relates to the use of a secretagogue, such as a ghrelin splice variant-like compound, in the treatment or prophylaxis of conditions, e.g., relating to neuronal damage and/or neurodegenerative disease and/or depression including a) prophylaxis or treatment of parkinson's disease, and/or b) prophylaxis or treatment of Alzheimer's disease, and/or c) prophylaxis or treatment of neuron degeneration, and/or d) prophylaxis or treatment of depression, and/or e) stimulation of neuron activity, fg. In particular, the present disclosure relates to the treatment or prophylaxis of parkinson's disease and/or prophylaxis of alzheimer's disease and/or the stimulation of neuron activity, prevention of neuron degeneration and/or the treatment or prophylaxis of depression, increasing quality of life, most preferably the prophylaxis or treatment of parkinson's disease and/or alzheimer's disease.

Neurodegenerative Disease

In accordance with the above, the compounds disclosed herein are particularly suitable for treating or preventing neuronal damage and/or neurodegenerative diseases in an individual suffering from the following Alzheimer's disease, Parkinson's disease, Huntington's disease, Amyotrophic lateral sclerosis (ALS), Aging. In another preferred embodiment, a secretagogue, such as ghrelin splice variant or a ghrelin splice variant-like compound, is used in the treatment or prevention of neuronal damage and/or neurodegenerative disease, Alzheimer's disease, Parkinson's disease, Huntington's disease, Amyotrophic lateral sclerosis (ALS), Aging. In one preferred embodiment, the individual treated for neuronal damage and/or neurodegenerative disease is elderly, such as 60-120 years old, such as 70-120 years old, such as 80-120 years old, such as 90-120 years old. Equally preferable are embodiments where said individual is a child, such as from 0-20 years old, such as 0-15 years old, such as 0-10 years old, such as 0-5 years old, such as 0-1 years old, such as a newborn child less than 2 months old.

In one embodiment, it is preferred that the secretagogue, such as a ghrelin splice variant-like compound, is administered prophylactically for preventing a neurodegenerative state. In this embodiment, the treatment may be started before any anti-neurodegenerative treatment initiates. The secretagogue may be administered continuously during the anti-neurodegenerative treatment, or it may be administered at intervals, for example between periods with anti-neurodegenerative therapy. By administering during and in particular between the periods of anti-neurodegenerative therapy, the risk that the treated individual acquires infections and/or other complications may be reduced due to better health conditions of the individual.

Treatment of neuronal damage and/or neurodegenerative disease using a secretagogue, such as ghrelin splice variant or a ghrelin splice variant-like compound, may be achieved using any administration method known in the art. Preferably, treatment may be achieved using any of the administration methods described herein, more preferably using intravenous or subcutaneous administration, most preferably using subcutaneous administration methods.

Subcutaneous Administration

It is important to note that ghrelin and ghrelin splice variant activate the GHS receptors and additional yet to be identified receptors. These receptors are found on GH producing cells, in the hypothalamic centers for appetite control and in a number of additional places in the organism. In the CNS, these receptors are tuned to receiving signals from local ghrelin splice variant-containing neurons. Peripherally-secreted or artificially-administered ghrelin splice variants will reach such sites and will pass the blood brain barrier specifically activating the appropriate receptors and triggering a specific pathway. However, currently available "so-called" GH secretagogues, which are small organic compounds such as MK-0677 (Merck), generally targeted to bind the GHS receptor will pass the blood brain barrier and also reach these sites, activating various GHS receptor related pathways and consequently having the danger of causing unwanted side effects such as dizziness, nausea, falling, elevated fasting serum glucose and insulin, and blurred vision. Thus, such compounds which do have the advantage of being, for example, orally active will not be optimal for mimicking the natural pre-meal, appetite-inducing surge of ghrelin splice variant, since they will activate non-specifically all GHS receptor related pathways in the body. In contrast, by using the natural peptide, ghrelin splice variant itself, or homologues thereof, and administering it peripherally—as in a preferred embodiment—it is ensured that only the relevant, appetite-regulating ghrelin splice variant receptors and pathways are reached and stimulated.

Any parenteral administration form that will ensure that the ghrelin splice variant receptors which normally are the target for peripherally-produced ghrelin splice variant in the pre-meal situation will be exposed to sufficient levels of the bioactive form of ghrelin splice variant to ensure robust and appropriate appetite stimulation, without causing desensitization of the system, may be part of an embodiment of the present disclosure. However, taking into consideration that the individuals to be treated possibly will have to receive treatment for a longer period, such as weeks or months, it is preferred that the administration form is well-suited thereto. Accordingly, it is preferred that the secretagogue, such as a ghrelin splice variant-like compound, is administered subcutaneously in an amount allowing sufficient levels of the bioactive form of ghrelin splice variant, i.e. the acylated form, to reach the receptors prior to the forthcoming meal.

The present disclosure preferably deals with methods for administering a secretagogue, such as ghrelin splice variant, in a way which mimics the physiologically pre-meal situation as closely as possible yet provides patients in need of increased food intake, for example fragile elderly, post-operative patients, and/or patients with lost appetite as part of neuronal damage and/or neurodegenerative disease for example precipitated by Parkinson's disease, Alzheimer's disease, etc., with a sufficient extra stimulatory input to their appetite-regulating ghrelin splice variant receptors, which normally are reached by ghrelin splice variant in the pre-meal situation.

Bolus Administration

Furthermore, from a molecular pharmacological point-of-view, it is important to note that it has been found that the ghrelin receptor, and therefore ghrelin splice variant receptor, normally is exposed to short-lived surges in ghrelin concentration. The GHS-R 1a receptor (growth hormone secretagogue receptor 1a) belongs to the class of G protein coupled receptors or 7TM receptors, which upon continued exposure to an agonist will be desensitized, internalized, and down-regulated. These mechanisms, which are inherent to the overall signal transduction system, involve processes such as receptor phosphorylation (which, in itself, decreases the affinity of the receptor for the agonist) and binding of inhibitory proteins such as arrestin (which sterically block the binding of signal transduction molecules such as G proteins). Another part of the agonist-mediated desensitization process is receptor internalization (i.e. physical removal of the receptor from the cell surface where it could bind the agonist) as well as receptor down regulation (i.e. decreased production/expression of the receptor). Receptor internalization could, after short-lived exposure of the receptor to agonist, be followed by a re-sensitization process, where the receptor is dephosphorylated and recycled to the cell surface to be used again. Without being bound by theory, it is believed that, upon prolonged stimulation which would occur for example during a long-lasting continuous infusion of the agonist, the receptor down-regulation process ensures that the target cell is adjusted in its signal transduction system to this situation.

Optimal Administration

The present disclosure also provides a procedure for an optimal administration of ghrelin splice variant to patients in order to obtain a maximal response and to avoid, for example, desensitization mechanisms.

Accordingly, one aspect relates to administration of a secretagogue, such as a ghrelin splice variant-like compound, in boluses, preferably a bolus prior to each main meal. It has been found, in contrary to the prolonged administration processes in the prior art, that a bolus administration leads not only to stimulation of appetite, but also to stimulation of feed intake and more important to stimulation of weight gain. Without being bound by theory, it is believed that pre-meal subcutaneous injection, intravenous injection, or short-term infusions of appropriate doses of a secretagogue, such as ghrelin splice variant or a ghrelin splice variant-like compound, will ensure that a robust stimulation of appetite-inducing ghrelin splice variant receptors will be obtained with minimal constraint to, e.g., the mobility of the patient. Thus, for example, patients with hip fractures can, in the post-operative situation, be treated in the pre-meal period and, if required during the meal as such, be free to move around and participate in the important post-operative physicotherapeutic regimens. In one preferred embodiment, a secretagogue such as ghrelin splice variant or a ghrelin splice variant-like compound is administered as a bolus in an amount equivalent to 10 μg per kg body weight.

Ghrelin Splice Variant-Like Compound

Any secretagogue, such as ghrelin splice variant or a ghrelin splice variant-like compound, may be used in the presently disclosed methods. One preferred type of ghrelin splice variant-like compound described herein is a compound comprising a structure defined by Formula I: Z1-(X1)m-(X2)-(X3)n-Z2, wherein Z1 is an optionally present protecting group; each X1 is independently selected from a naturally occurring amino acid and a synthetic amino acid; X2 is selected from a naturally occurring amino acid and a synthetic amino acid, said amino acid being modified with a bulky hydrophobic group; each X3 is independently selected from a naturally occurring amino acid and a synthetic amino acid, wherein one or more of X1 and X3 optionally may be modified with a bulky hydrophobic group; Z2 is an Optionally present protecting group; m is an integer in the range of from 1-10; n is an integer in the range of from 4-92; provided that the compound according to formula Z1-(X1)m-(X2)-(X3)n-Z2 is 15-94 amino acids in length and has at least 80% (or, in alternative embodiments, 85%, 90%, 93%, 95%, 97%, 98%, 99%, 100%) homology to SEQ ID NO:1. In a preferred embodiment, the ghrelin splice variant-like compound is 22-29 amino acids in length.

Accordingly, the term "secretagogue" includes the naturally occurring 29 amino acid human ghrelin splice variant, the amino acid sequence of which is shown in SEQ ID NO:5, as well as the naturally occurring 22 amino acid human ghrelin splice variant, the amino acid sequence of which is shown in SEQ ID NO:2, and the naturally occurring, 24 amino acid human ghrelin splice variant, the sequence of which is shown in SEQ ID NO:3.

The present disclosure includes diastereomers as well as their racemic and resolved enantiomerically pure forms. Secretagogues can contain D-amino acids, L-amino acids, alpha-amino acid, beta-amino acid, gamma-amino acid, natural amino acid and/or synthetic amino acid or the like or a combination thereof. Preferably, amino acids present in a ghrelin splice variant-like compound are the L-enantiomers.

The ghrelin splice variant-like compound preferably comprises an amino acid modified with a bulky hydrophobic group. The number of amino acids N-terminal to the modified amino acid is preferably within the range of from 1-9. Accordingly, m is preferably an integer in the range of from 1-9, such as of from 1-8, such as of from 1-7, such as of from 1-6, such as of from 1-5, such as of from 1-4, such as of from 1-3, such as of from 1-2, such as 2.

It is more preferred that the number of amino acids N-terminally to the modified amino acid is low, such as of from 1-3, such as of from 1-2. Most preferably 2 amino acids are positioned N-terminal to the modified amino acid.

In a preferred embodiment, (X1)m has a Gly residue in the N-terminal part of the sequence. Accordingly, in preferred embodiment, (X1)m is selected from the sequences: Gly, Gly-Ser, Gly-Cys, Gly-Lys, Gly-Asp, Gly-Glu, Gly-Arg, Gly-His, Gly-Asn, Gly-Gln, Gly-Thr, and Gly-Tyr. More preferably (X1)m is selected from Gly-Ser and Gly-Cys; most preferably (X1)m is Gly-Ser.

In other words, in a preferred embodiment the ghrelin splice variant-like compound is selected from Z1-Gly-(X1)m-(X2)-(X3)n-Z2 (Formula II), Z1-Gly-Ser-(X2)-(X3)n-Z2 (Formula III), and Z1-Gly-(X2)-(X3)n-Z2 (Formula IV). More preferably, the ghrelin splice variant-like compound has Formula III.

As described above, X2 may be any amino acid modified with a bulky hydrophobic group. In particular, X2 is selected from the group consisting of modified Ser, modified Cys, modified Asp, modified Lys, modified Trp, modified Phe, modified Ile, and modified Leu. More preferably, X2 is selected from the group consisting of modified Ser, modified Cys, and modified Lys; most preferably X2 is modified Ser.

Furthermore, (X1)m-(X2) is preferably Gly-Xaa-Ser* or Gly-Xaa-Cys*, wherein Xaa is any amino acid, more preferably (X1)m-(X2) is Gly-Ser-Ser* or Gly-Ser-Cys*, wherein * indicates that the amino acid residue is modified with a bulky hydrophobic group.

(X3)n preferably comprises a sequence which is a fragment of ghrelin splice variant, such as human ghrelin splice variant. Accordingly, (X3)n preferably comprises a fragment of the following sequence (SEQ ID NO:6): Pile Leu Ser Pro Glu His Gln Arg Val Gln Val Arg Pro Pro His Lys Ala Pro His Val Val Pro Ala Leu Pro Len Ser Asn Gln Leu Cys Asp Leu Glu Gln Gln Arg His Leu Trp Ala Ser Val Phe Ser Gln Ser Thr Lys Asp Ser Gly Ser Asp Leu Thr Val Ser Gly Arg Thr Trp Gly Leu Arg Val Leu Asn Arg Len Phe Pro Pro Ser Ser Arg Glu Arg Ser Arg Arg Ser His Gln Pro Ser Cys Ser Pro Glu Leu.

In a preferred embodiment, the length of the ghrelin splice variant-like compound is substantially similar to the length of processed human ghrelin, i.e. 29 amino acids. Accordingly, n is preferably an integer in the range of from 4 to 25, such as of from 4 to 24, such as of from 4 to 22, such as of from 4 to 15, such as of from 4 to 10 such as of from 10 to 25, such as of from 10 to 24, such as of from 15 to 25, such as of from 15 to 24. Most preferably, a ghrelin splice variant-like compound is the 29 amino acid human ghrelin splice variant, the amino acid sequence of which is shown in SEQ ID NO:5; is the 22 amino acid human ghrelin splice variant, the amino acid sequence of which is shown in SEQ ID NO:2; is the 24 amino acid human ghrelin splice variant, the amino acid sequence of which is shown in SEQ ID NO:3; or is the 24 amino acid human ghrelin splice variant having a 2,3-diaminopropionic acid (Dpr) residue in the third position, the amino acid sequence of which is shown in SEQ ID NO:4.

Functionality

The secretagogues described herein are active at the receptor for GHS as described above, i.e. the receptor GHS-R 1a. The compounds can bind to GHS-R 1a, and preferably, stimulate receptor activity. In some embodiments, the compounds can bind other receptors and, optionally, stimulate their activity.

Receptor activity can be measured using different techniques such as detecting a change in the intracellular conformation of the receptor, in the G-protein coupled activities, and/or in the intracellular messengers. One simple measure of the ability of a ghrelin splice variant-like compound to activate the ghrelin splice variant receptor is to measure its EC50, i.e. the dose at which the compound is able to activate the signaling of the receptor to half of the maximal effect of the compound. When measuring, e.g., EC50, the receptor can either be expressed endogenously on primary cell cultures, for example pituitary cells, or heterologously expressed on cells transfected with the ghrelin receptor. Whole cell assays or assays using membranes prepared from either of these cell types can be used depending on the type of assay.

As the receptor is generally believed to be primarily coupled to the Gq signaling pathway, any suitable assay which monitors activity in the Gq/G11 signaling pathway can be used, for example:

1) An assay measuring the activation of Gq/G11 performed, for example, by measurement of GTPgS binding combined with, e.g., anti-G-alpha-q or −11 antibody precipitation in order to increase the signal to noise ratio. This assay may also detect coupling to other G-proteins than Gq/11.

2) An assay which measures the activity of phospholipase C (PLC), one of the first down-stream effector molecules in the pathway, for example by measuring the accumulation of inositol phosphate which is one of the products of PLC.

3) More down stream in the signaling cascade is the mobilization of calcium from the intracellular stores, which can be measured by any method known to one of ordinary skill in the art.

4) Even more down stream, signaling molecules such as the activity of different kinds of MAP kinases (p38, jun, etc.), NfκB translocation and CRE driven gene transcription may also be measured.

5) Binding of fluorescently-tagged arrestin to the activated ghrelin receptor.

Examples of suitable protocols for use in determining secretagogue functionality are given in Example 4, infra.

In one embodiment, the binding of a compound to the receptor GHS-R 1a can be measured by the use of the assay described herein above.

A ghrelin splice variant-like compound preferably has at least about: 50%, at least about 60%, at least about 70%, at least about 80%, or at least about 90%, functional activity relative to the 28 amino acid human wild-type ghrelin as determined using an assay described herein above, and/or an EC50 greater than about 1,000, greater than about 100, or greater than about 50, or greater than about 10. Greater refers to potency and thus indicates a lesser amount is needed to achieve binding inhibition.

In one embodiment, the compound has potency (EC50) on the GHS-R 1a of less than 500 nM. In another embodiment the compound has a potency (EC50) on the GHS-R 1a of less than 100 nM, such as less than 80 nM, such as less than 60 nM, such as less than 40 nM, such as less than 20 nM, such as less than 10 nM, such as less than 5 nM, such as less than 1 nM, such as less than 0.5 nM, such as less than 0.1 nM, such as less than 0.05 nM, such as less than 0.01 nM.

In a further embodiment, the dissociation constant (Kd) of the compound is less than 500 nM. In a still further embodiment the dissociation constant (Kd) of the ligand is less than 100 nM, such as less than 80 nM, such as less than 60 nM, such as less than 40 nM, such as less than 20 nM, such as less than 10 nM, such as less than 5 nM, such as less than 1 nM, such as less than 0.5 nM, such as less than 0.1 nM, such as less than 0.05 nM, such as less than 0.01 nM.

Binding assays can be performed using recombinantly-produced receptor polypeptides present in different environments. Such environments include, for example, cell extracts and purified cell extracts containing the receptor polypeptide expressed from recombinant nucleic acid or naturally occurring nucleic acid, and also include, for example, the use of a purified GHS receptor polypeptide produced by recombinant means or from naturally occurring nucleic acid which is introduced into a different environment.

Using a recombinantly expressed GHS receptor offers several advantages, such as the ability to express the receptor in a defined cell system, so that a response to a compound at the receptor can more readily be differentiated from responses at other receptors. For example, the receptor can be expressed in a cell line such as HEK 293, COS 7, and CHO not normally expressing the receptor by an expression vector, wherein the same cell line without the expression vector can act as a control.

Identity and Homology

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, Madison, Wis.). This software matches similar sequences by assigning degrees of homology to various substitutions, deletions, and other modifications.

A ghrelin splice variant homologue of one or more of the sequences specified herein may vary in one or more amino acids as compared to the sequences defined, but is capable of performing the same function, i.e. a homologue may be envisaged as a functional equivalent of a predetermined sequence.

A ghrelin splice variant homologue is preferably a ghrelin splice variant-like compound as defined above.

As described above, a homologue of any of the predetermined sequences herein may be defined as i) homologues comprising an amino acid sequence capable of being recognized by an antibody, said antibody also recognizing the 22 amino acid and/or the 24 amino acid human ghrelin splice variant and/or the 29 amino acid human ghrelin splice variant, preferably the acylated 22 amino acid and/or the 24 amino acid human ghrelin splice variant and/or the 29 amino acid human ghrelin splice variant, and/or ii) homologues comprising an amino acid sequence capable of binding selectively to GHS-R 1a, and/or iii) homologues having a substantially similar or higher binding affinity to GHS-R 1a than the 22 amino acid and/or the 24 amino acid human ghrelin splice variant and/or the 29 amino acid human ghrelin splice variant, preferably the acylated 22 amino acid and/or the 24 amino acid human ghrelin splice variant and/or the 29 amino acid human ghrelin splice variant. (The 22 amino acid and/or the 24 amino acid and/or the 29 amino acid human ghrelin splice variant can have the sequence shown in SEQ ID NO:2, SEQ ID NO:3, SEQ ID NO:4, or SEQ ID NO:5, and, when acylated, is acylated at position 3.)

The antibodies used herein may be antibodies binding the N-terminal region of ghrelin splice variant or the C-terminal region of ghrelin splice variant, preferably the N-terminal region. The antibodies may be antibodies as described in Ariyasu H. et al., Endocrinology 143:3341-50 (2002).

Exemplary homologues comprise one or more conservative amino acid substitutions including one or more conservative amino acid substitutions within the same group of predetermined amino acids, or a plurality of conservative amino acid substitutions, wherein each conservative substitution is generated by substitution within a different group of predetermined amino acids. Homologues may thus comprise conservative substitutions independent of one another, wherein at least one glycine (Gly) of said homologue is substituted with an amino acid selected from the group of amino acids consisting of Ala, Val, Leu, and Ile, and independently thereof, homologues, wherein at least one of said alanines (Ala) of said homologue thereof is substituted with an amino acid selected from the group of amino acids consisting of Gly, Val, Leu, and Ile; and, independently thereof, homologues wherein at least one valine (Val) of said homologue thereof is substituted with an amino acid selected from the group of amino acids consisting of Gly, Ala, Leu, and Ile; and, independently thereof, homologues wherein at least one of said leucines (Leu) of said homologue thereof is substituted with an amino acid selected from the group of amino acids consisting of Gly, Ala, Val, and Ile; and, independently thereof, homologues wherein at least one isoleucine (Ile) of said homologues thereof is substituted with an amino acid selected from the group of amino acids consisting of Gly, Ala, Val and Leu; and, independently thereof, homologues wherein at least one of said aspartic acids (Asp) of said homologue thereof is substituted with an amino acid selected from the group of amino acids consisting of Glu, Asn, and Gln; and, independently thereof, homologues wherein at least one of said phenylalanines (Phe) of said homologues thereof is substituted with an amino acid selected from the group of amino acids consisting of Tyr, Trp, His, and Pro, and preferably selected from the group of amino acids consisting of Tyr and Trp; and, independently thereof, homologues wherein at least one of said tyrosines (Tyr) of said homologues thereof is substituted with an amino acid selected from the group of amino acids consisting of Phe, Trp, His, and Pro, preferably an amino acid selected from the group of amino acids consisting of Phe and Trp; and, independently thereof, homologues wherein at least one of said arginines (Arg) of said fragment is substituted with an amino acid selected from the group of amino acids consisting of Lys and His; and, independently thereof, homologues wherein at least one lysine (Lys) of said homologues thereof is substituted with an amino acid selected from the group of amino acids consisting of Arg and His; and, independently thereof, homologues wherein at least one of said asparagines (Asn) of said homologues thereof is substituted with an amino acid selected from the group of amino acids consisting of Asp, Glu, and Gln; and, independently thereof, homologues wherein at least one glutamine (Gln) of said homologues thereof is substituted with an amino acid selected from the group of amino acids consisting of Asp, Gln, and Asn; and, independently thereof, homologues wherein at least one proline (Pro) of said homologues thereof is substituted with an amino acid selected from the group of amino acids consisting of Phe, Tyr, Trp, and His; and, independently thereof, homologues wherein at least one of said cysteines (Cys) of said homologues thereof is substituted with an amino acid selected from the group of amino acids consisting of Asp, Glu, Lys, Arg, His, Asn, Gln, Ser, Thr, and Tyr.

Conservative substitutions may be introduced in any position of a preferred predetermined sequence. It may however also be desirable to introduce non-conservative substitutions, particularly, but not limited to, a non-conservative substitution in any one or more positions.

A non-conservative substitution leading to the formation of a functionally equivalent homologue of the sequences herein would for example i) differ substantially in polarity, for example a residue with a non-polar side chain (Ala, Leu, Pro, Trp, Val, Ile, Gly, Leu, Phe or Met) substituted for a residue with a polar side chain such as Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include, for example, arginine and lysine; glutamate and aspartate; serine and threonine; glutamine and asparagine; and valine, leucine, and isoleucine.

In a preferred embodiment, the binding domain comprises a homologue having an amino acid sequence at least 60% homologous to SEQ ID NO:1. More preferably the homology is at least 65%, such as at least 70% homologous, such as at least 75% homologous, such as at least 80% homologous, such as at least 85% homologous, such as at least 90% homologous, such as at least 95% homologous, such as at least 98% homologous to SEQ ID NO:1. In a more preferred embodiment, the percentages mentioned above relate to the identity of the sequence of a homologue as compared to SEQ ID NO:1. Homologues to SEQ ID NO:1 may be 22 amino acid human ghrelin splice variant (SEQ ID NO:2), 24 amino acid human ghrelin splice variant (SEQ ID NO:3), or 29 amino acid human ghrelin splice variant (SEQ ID NO:5). Other homologues are the variants described in EP 1 197 496 (Kangawa), incorporated herein by reference.

Bulky Hydrophobic Group

The bulky hydrophobic group of secretagogues disclosed herein is any bulky hydrophobic group capable of providing the des-acylated 28 amino acid human wild-type ghrelin, or an analogue thereof, with binding affinity to GHS-R 1a and or GS-R-1b. Any suitable amino acid may be modified with any suitable bulky hydrophobic group. In a preferred embodiment, a Ser residue (preferably, amino acid number 3 in the ghrelin splice variant amino acid chain) is modified with the bulky hydrophobic group. When the amino acid being modified contains, e.g., —OH, —SH, —NH or —$NH_2$ as a substituent group in a side chain thereof, a group formed by acylating such a substituent group is preferred. The mode of linkage may thus be selected from the group consisting of ester, ether, thioester, thioether, amide and carbamide. For example, if the modified amino acid is serine, threonine, tyrosine or oxyproline, the amino acid has a hydroxyl group in the side chain. If the modified amino acid is cysteine, the amino acid has a mercapto group in the side chain. If the modified amino acid is lysine, arginine, histidine, tryptophan, proline or oxyproline, it has an amino group or imino group in the side chain.

The hydroxyl group, mercapto group, amino group and imino group described above may thus be chemically modified. That is, the hydroxyl group or mercapto group may be, for example, etherized, esterified, thioetherified or thioesterified. The imino group may be, for example, iminoetherified, iminothioetherified or alkylated. The amino group may be, for example, amidated thioamidated or carbamidated. Further, the mercapto group may be, for example, disulfidated; the imino group may be, for example, amidated or thioamidated; and the amino group may be, for example, alkylated or thiocarbamidated.

In a preferred embodiment, the modified amino acid is Ser coupled through an ester linkage to the hydrophobic group or, in another preferred embodiment, the modified amino acid is Dpr coupled through an amide, linkage to the hydrophobic group.

The hydrophobic group may be any group with a saturated or unsaturated alkyl or acyl group containing one or more carbon atoms. In one embodiment, the bulky hydrophobic group is an acyl group, including groups formed by removing a hydroxyl group from an organic carboxylic acid, organic sulfonic acid or organic phosphoric acid. The organic carboxylic acid includes, e.g., fatty acids, and the number of carbon atoms thereof is preferably 1 to 35. In the organic sulfonic acid or organic phosphoric acid, the number of carbon atoms thereof is preferably 1 to 35.

Accordingly, the acyl group is preferably selected from a $C_1$-$C_{35}$ acyl group, such as a $C_1$-$C_{20}$ acyl group, such as a $C_1$-$C_{15}$ acyl group, such as a $C_6$-$C_{15}$ acyl group, such as a $C_6$-$C_{12}$ acyl group, such as a $C_8$-$C_{12}$ acyl group. More preferably, the acyl group is selected from the group consisting of $C_7$ acyl group, $C_8$ acyl group, $C_9$ acyl group, $C_{10}$ acyl group, $C_{11}$ acyl group, and $C_{12}$ acyl group. Such acyl group may be formed from octanoic acid (preferably caprylic acid), decanoic acid (preferably capric acid), or dodecanoic acid (preferably lauric acid), as well as monoene or polyene fatty acids thereof.

Furthermore, the modified amino acid may be any amino acid wherein a group is modified as described in EP 1 197 496 (Kangawa), which is hereby incorporated by reference.

Protecting Group

The ghrelin splice variant-like compound according to the present disclosure may comprise a protecting group at the N-terminus or the C-terminus or at both. A protecting group covalently joined to the N-terminal amino group reduces the reactivity of the amino terminus under in vivo conditions. Amino protecting groups include, for example, $C_1$-$C_{10}$ alkyl, $C_1$-$C_{10}$ substituted alkyl, $C_2$-$C_{10}$ alkenyl, $C_2$-$C_{10}$ substituted alkenyl, aryl, $C_1$-$C_6$ alkyl aryl, C(O)—(CH$_2$)—($C_1$-$C_6$ alkyl)-COOH, C(O)—($C_1$-$C_6$ alkyl). C(O)-aryl, C(O)—O—($C_1$-$C_6$-alkyl), or C(O)—O-aryl. Preferably, the amino terminus protecting group is acetyl, propyl, succinyl, benzyl, benzyloxycarbonyl or t-butyloxycarbonyl.

A protecting group covalently joined to the C-terminal carboxy group reduces the reactivity of the carboxy terminus under in vivo conditions. The carboxy terminus protecting group is preferably attached to the a-carbonyl group of the last amino acid. Carboxy terminus protecting groups include, for example, amide, methylamide, and ethylamide.

Conjugates

The secretagogue, such as a ghrelin splice variant-like compound, may be provided in the form of a secretagogue conjugate, i.e. a molecule comprising the secretagogue conjugated to another entity. The other entity may be any substance that is capable of conferring improved properties to the secretagogue, e.g. in terms of improved stability, half-life, etc. Examples of suitable entities are described in the following. For example, the secretagogue may be conjugated to a peptide, such as a peptide having effect on nociceptin receptor ORL1. In one embodiment, the conjugate is a conjugate of ghrelin splice variant or a derivative or homologue thereof and a peptide having effect on ORL1, e.g. the peptide Ac-RYY (RK) (WI) RK)-NH$_2$, where the brackets show allowable variation of amino acid residues. Examples of other suitable peptides are found in Published U.S. Patent Application Nos. 2003/040472 and 2002/004483, and U.S. Pat. No. 5,869,046, each of which is incorporated herein by reference.

In another embodiment, a secretagogue, such as ghrelin splice variant or a ghrelin splice variant-like compound, is conjugated to a polymer molecule. The polymer molecule may be any suitable polymer molecule, such as a natural or synthetic polymer, typically with a molecular weight in the range of about 1-100 kDa, such as about 3-20 kDa, such as 5-10 kDa. The polymer is attached to a reactive group present on the secretagogue, e.g. an amine group or a thiol group. Examples of suitable polymer molecules include polymer molecules selected from the group consisting of polyalkylene oxide (PAO)), including polyalkylene glycol (PAG), such as linear or branched polyethylene glycol (PEG) and polypropylene glycol (PPG); poly-vinyl alcohol (PVA); poly-carboxylate; poly-(vinylpyrolidorte); polyethylene-co-maleic acid anhydride; polystyrene-co-maleic acid anhydride; and dextran, including carboxymethyl-dextran. Preferably, the polymer molecule is a PEG molecule, in particular a monofunctional PEG, such as methoxypolyethylene glycol (mPEG). Suitable activated PEG molecules are available from, for example, Nektar Therapeutics Inc. (Huntsville, Ala.) or Valentis, Inc. (Burlingame, Calif.). Alternatively, the polymer molecules can be activated by conventional methods known in the art, e.g., as disclosed in WO 90/13540, incorporated herein by reference. Specific examples of activated PEG polymers include the following linear PEGs: NHS-PEG (e.g., SPA-PEG, SSPA-PEG, SBA-PEG, SS-PEG, SSA-PEG, SC-PEG, SG-PEG, and SCM-PEG), NOR-PEG, BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. Nos. 5,932,462 and 5,643,575, both of which are incorporated herein by reference.

The PEGylation (i.e., conjugation of the secretagogue polypeptide and the activated polymer molecule is conducted in accordance with established procedures, e.g., as described in the following references (which also describe suitable methods for activation of polymer molecules): R. F. Taylor, (1991), "Protein Immobilization, Fundamentals and Applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.).

It is also contemplated according to the present disclosure to couple the polymer molecules to the secretagogue through a linker. Suitable linkers are well known to the skilled person. A preferred example is cyanuric chloride (Abuchowski A. et al., J. Biol. Chem. 252:3578-81 (1977); U.S. Pat. No. 4,179,337; Shafer et al., J. Polym. Sci. Polym. Chem. Ed. 24:375-78 (1986)).

In yet another embodiment, the secretagogue is conjugated to an oligosaccharide molecule, such as dextran, glycan, transferrin, etc. Such conjugation may be achieved in accordance with established technologies, e.g. those available from Neose Technologies, Inc. (Horsham, Pa.).

In yet another embodiment, the secretagogue is conjugated to an Fc region of an IgG molecule, typically in die form of a fusion protein. For instance, a salvage receptor binding epitope of the Fc region of an IgG3 (i.e. the Fc portion of an immunoglobulin of the isotype IgG) is incorporated into the secretagogue so as to increase its circulatory half-life, but so as not to lose its biological activity. This can take place by any means, such as by mutation of the appropriate region in the secretagogue to mimic the Fc region or by incorporating the epitope into a peptide tag that is then fused to the secretagogue at either end or in the middle or by DNA or peptide synthesis.

The salvage receptor binding epitope is any suitable such epitope as known to the person skilled in the art, and its nature will depend, e.g., on the type of secretagogue being modified. The epitope is introduced into the secretagogue such that the biological activity of the secretagogue is maintained, i.e., the epitope does not adversely affect the conformation of the secretagogue or affect its binding to ligands that confers its biological activity.

Alternatively to providing the secretagogue in the form of a conjugate, the secretagogue may be modified to include suitable reactive groups, whereby the thus modified secretagogue is capable of forming a conjugate in vivo (after having been administered to an individual) through covalent bonding with available reactive functionalities on blood components. The present disclosure also relates to such modified secretagogues, and methods for their use. Also, the present disclosure relates to conjugates formed in vitro between a modified secretagogue as described above and a blood component. The conjugates formed in accordance with this embodiment are contemplated to have an increased in vivo half life as compared to the corresponding non-modified secretagogue.

In accordance with this embodiment, the secretagogue is modified with a chemically reactive group (reactive entity). The reactive entity may, e.g., be selected from the wide variety of active carboxyl groups, particularly esters, where the hydroxyl moiety is physiologically acceptable. Such groups may be selected from the group consisting of N-hydroxysuccinimide (NHS), N-hydroxy-sulfosuccinimide (sulfo-NHS), maleimide-benzoyl-succinimide (MBS), gamma-maleimido-butyryloxy succinimide ester (GMBS) and maleimidopropionic acid (MPA). The principal targets for this group of entities are primary amines on the blood component. Another group of active entities is constituted by a maleimido-containing group such as MPA and gamma-maleimide-butrylamide (GMBA). Such groups react with thiol groups present on the blood component (Lee V. H. L. in "Peptide and Protein Drug Delivery", New York, N.Y., M. Dekker, 1990).

The blood component with which the modified secretagogue is designed to react may be any blood component having an available target group, e.g. an amine or a thiol group, and which is suitable as a carrier for binding the modified secretagogue in vivo and thereby extend the circulating half-life thereof. Examples of such blood components are serum albumin and IgG.

As mentioned above, the covalent bonding of a modified secretagogue to a blood component may be achieved in vivo by administration of the modified secretagogue directly to the patient. The administration may be done in any suitable form, such as in the form of a bolus or introduced slowly over time by infusion using metered flow or the like. Alternatively, the secretagogue/blood component conjugate may also be prepared ex vivo by combining blood with the modified secretagogue, allowing covalent bonding of the modified secretagogue to reactive functionalities on blood components and then returning or administering the conjugated blood to the individual.

Moreover, the above may also be accomplished by first purifying an individual blood component or limited number of components, such as red blood cells, immunoglobulins, serum albumin, or the like, and combining the component or components ex vivo with the chemically reactive secretagogues.

Production of Ghrelin Splice Variant-Like Compounds

Ghrelin splice variant-like compounds can be produced using techniques well known in the art. For example, a polypeptide region of a ghrelin splice variant-like compound can be chemically or biochemical synthesized and modified. Techniques for chemical synthesis of polypeptides are well known in the art (see, e.g., Lee V. H. L. in "Peptide and Protein Drug Delivery", New York, N.Y., M. Dekker, 1990). Examples of techniques for biochemical synthesis involving the introduction of a nucleic acid into a cell and expression of nucleic acids are provided in Ausubel et al., "Current Protocols in Molecular Biology", John Wiley, 1987-1998, and Sambrook J. et al., "Molecular Cloning, A Laboratory Manual", 2d Edition, Cold Spring Harbor Laboratory Press, 1989, each of which is incorporated herein by reference. Another exemplary technique, described in U.S. Pat. No. 5,304,489, incorporated herein by reference, is the use of a transgenic mammals having mammary gland-targeted mutations which result in the production and secretion of synthesized ghrelin splice variant-like compound in the milk of the transgenic mammal.

The ghrelin splice variant-like compounds can also be recombinantly produced using routine expression methods known in the art. The polynucleotide encoding the desired ghrelin splice variant-like compound is operably linked to a promoter into an expression vector suitable for any convenient host. Both eukaryotic and prokaryotic host systems are used in forming recombinant ghrelin splice variant-like compounds. The ghrelin splice variant-like compound is then isolated from lysed cells or from the culture medium and purified to the extent needed for its intended use.

Consequently, a further embodiment is for a method of producing a ghrelin splice variant-like compound, said method comprising the steps of: (a) providing a cDNA comprising a polynucleotide sequence encoding a ghrelin splice variant-like compound; (b) inserting said cDNA in an expression vector such that the cDNA is operably linked to a promoter; and (c) introducing said expression vector into a host cell whereby said host cell produces said ghrelin splice variant-like compound.

In one aspect of this embodiment, the method further comprises the step of recovering the ghrelin splice variant-like compound produced in step (c). Another embodiment is a ghrelin splice variant-like compound obtainable by the method described in the preceding paragraph. The expression vector is any of the mammalian, yeast, insect, or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained in U.S. Pat. No. 5,082,767, which disclosure is hereby incorporated by reference in its entirety.

In another embodiment, it is often advantageous to add to the recombinant polynucleotide additional nucleotide sequence(s) which codes for secretory or leader sequences, pro-sequences, sequences which aid in purification, such as multiple histidine residues, or an additional sequence for stability during recombinant production.

Introduction of a polynucleotide encoding a ghrelin splice variant-like compound into a host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., (1986) Basic Methods in Molecular Biology, ed., Elsevier Press, NY, which disclosure is hereby incorporated by reference in its entirety. It is specifically contemplated that the ghrelin splice variant-like compounds disclosed herein may in fact be expressed by a host cell lacking a recombinant vector or naturally produced by a cell.

Ghrelin splice variant-like compounds can be recovered and purified from recombinant cell cultures by well-known methods including differential extraction, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography (see, for example, "Methods in Enzymology: Aqueous Two-Phase Systems", Walter H et al. (eds.), Academic Press (1993), incorporated herein by reference, for a variety of methods for purifying proteins). In one embodiment, high performance liquid chromatography ("HPLC") is employed for purification. A recombinantly produced version of a ghrelin splice variant-like compound can be substantially purified using techniques described herein or otherwise known in the art, such as, for example, by the one-step method described in Smith & Johnson, Gene 67:31 40 (1988), which disclosure is hereby incorporated by reference in its entirety. Ghrelin splice variant-like compounds also can be purified from recombinant sources using antibodies directed against the ghrelin splice variant-like compounds, such as those described herein, in methods which are well known in the art of protein purification.

In one embodiment, the recombinantly expressed ghrelin splice variant-like compound is purified using standard immunochromatography techniques. In such procedures, a solution containing the ghrelin splice variant-like compound of interest, such as the culture medium or a cell extract, is applied to a column having antibodies against the ghrelin splice variant-like compound attached to the chromatography matrix. The recombinant ghrelin splice variant-like compound is allowed to bind the immunochromatography column. Thereafter, the column is washed to remove non-specifically bound proteins. The specifically bound secreted ghrelin splice variant-like compound is then released from the column and recovered using standard techniques.

Depending upon the host employed in a recombinant production procedure, the ghrelin splice variant-like compounds may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Pharmaceutical Compositions

While it is possible for the compounds or salts of the present disclosure to be administered as the raw chemical, it is preferred to present them in the form of a pharmaceutical composition. Accordingly, one aspect relates to a pharmaceutical composition comprising a ghrelin splice variant-like compound as defined in Formula I.

Another embodiment relates to a pharmaceutical composition comprising a mixture of at least two different ghrelin splice variant-like compounds, such as a mixture of a ghrelin splice variant-like compound acylated with a $C_8$ acyl and a ghrelin splice variant-like compound acylated with a $C_{10}$ acyl. Without being bound by theory, it is believed that such a mixture will have a longer half-life in plasma.

In yet another embodiment, the pharmaceutical composition comprises acylated ghrelin splice variant-like compounds, optionally compounds having different acyl chain lengths preferably selected from the group consisting of $C_7$ acyl group, $C_9$ acyl group, and $C_{11}$ acyl group, optionally in combination with a desacylated ghrelin splice variant-like compound.

Another aspect relates to a pharmaceutical composition comprising any secretagogue, such as any ghrelin splice variant-like compound as defined above or a pharmaceutically acceptable salt thereof and pharmaceutical acceptable carriers, vehicles and/or excipients; said composition farther comprising transport molecules. The transport molecules are primarily added in order to increase the half-life of the acylated compound, preventing premature des-acylation, since the des-acylated ghrelin splice variant might not be active at the GHS-R 1a.

Transport molecules act by having incorporated into or anchored to it a compound disclosed herein. Any suitable transport molecule known to the skilled person may be used. Examples of transport molecules are those described in the conjugate section, supra. Other preferred examples are liposomes, micelles, and/or microspheres.

Conventional liposomes are typically composed of phospholipids (neutral or negatively charged) and/or cholesterol. The liposomes are vesicular structures based on lipid bilayer surrounding aqueous compartments. They can vary in their physio-chemical properties such as size, lipid composition, surface charge and number, and fluidity of the phospholipids bilayer. The most frequently used lipids for liposome formation are: 1,2-Dilautroyl-sn-Glycero-3-Phosphocholine (DLPC), 1,2-Dimyristoyl-sn-Glycero-3-Phosphocholine (DMPC), 1,2-Dipalmitoyl-sn-Glycero-3-Phosphocholine (DPPC), 1,2-Distearoyl-sn-Glycero-3-Phosphocholine (DSPC), 1,2-Dioleoyl-sn-Glycero-3-Phosphocholine (DOPC), 1,2-Dimyristoyl-sn-Glycero-3-Phosphoethanolamine (DMPE), 1,2-Dipalmitoyl-sn-Glycero-3-Phosphoethanolamine (DPPE), 1,2-Dioleoyl-sn-Glycero-3-Phosphoethanolamine (DOPE), 1,2-Dimyristoyl-sn-Glycero-3-Phosphate (Monosodium Salt) (DMPA), 1,2-Dipalmitoyl-sn-Glycero-3-Phosphate (Monosodium Salt) (DPPA), 1,2-Dioleoyl-sn-Glycero-3-Phosphate (Monosodium Salt) (DOPA), 1,2-Dimyristoyl-sn-Glycero-3-[Phospho-rac-(1-glycerol] (Sodium Salt) (DMPG), 1,2-Dipalmitoyl-sn-Glycero-3-[Phospho-rac-(1-glycerol)] (Sodium Salt) (DPPG), 1,2-Dioleoyl-sn-Glycero-3-[Phospho-rac-(1-glycerol)] (Sodium Salt) (DOPG), 1,2-Dimyristoyl-sn-Glycero-3-[Phospho-L-Serine] (Sodium Salt) (DMPS), 1,2-Dipalmitoyl-sn-Glycero-3-[Phospho-L-Serine] (Sodium Salt) (DPPS), 1,2-Dioleoyl-sn-Glycero-3-[Phospho-L-Serine] (Sodium Salt) (DOPS), 1,2-Dioleoyl-sn-Glycero-3-Phosphoethanolamine-N-(glutaryl) (Sodium Salt) and 1,1',2,2'-Tetramyristoyl Cardiolipin (Ammonium Salt). Formulations composed of DPPC in combination with other lipid or modifiers of liposomes are preferred, e.g., in combination with cholesterol and/or phosphatidylcholine.

Long-circulating liposomes are characterized by their ability to extravasate at body sites where the permeability of the vascular wall is increased. A preferred way to produce long circulating liposomes is to attach hydrophilic polymer polyethylene glycol (PEG) covalently to the outer surface of the liposome. Some of the preferred lipids are: 1,2-Dipalmitoyl-sn-Glycero-3-Phosphoethanolamine-N-[Methoxy (Polyethylene glycol)-2000] (Ammonium Salt), 1,2-Dipalmitoyl-sn-Glycero-3-Phosphoethanolamine-N-[Methoxy (Polyethylene glycol)-5000] (Ammonium Salt), 1,2-Dioleoyl-3-Trimethylammonium-Propane (Chloride Salt) (DOTAP).

Possible lipids applicable for liposomes are supplied by Avanti Polar Lipids, Inc., (Alabaster, Ala.). Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

A variety of methods are available for preparing liposomes, as described in, e.g., Szoka F. & Papahadjopolous D., Ann. Rev. Biophys. Bioeng. 9:467-508 (1980); U.S. Pat. Nos. 4,235,871, 4,501,728 and 4,837,028; all of which are incorporated herein by reference.

Another method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

Micelles are formed by surfactants (molecules that contain a hydrophobic portion and one or more ionic or otherwise strongly hydrophilic groups) in aqueous solution. As the concentration of a solid surfactant increases, its monolayers adsorbed at the air/water or glass/water interface become so tightly packed that further occupancy requires excessive compression of the surfactant molecules already in the two monolayers. Further increments in the amount of dissolved surfactant beyond that concentration cause amounts equivalent to the new molecules to aggregate into micelles. This process begins at a characteristic concentration called "critical micelle concentration".

The shape of micelles formed in dilute surfactant solutions is approximately spherical. The polar head groups of the surfactant molecules are arranged in an outer spherical shell whereas their hydrocarbon chains are oriented toward the center, forming a spherical core for the micelle. The hydrocarbon chains are randomly coiled and entangled and the micellar interior has a nonpolar, liquid-like character. In the micelles of polyoxyethylated nonionic detergents, the polyoxyethlene moieties are oriented outward and permeated by water. This arrangement is energetically favorable since the hydrophilic head groups are in contact with water and the hydrocarbon moieties are removed from the aqueous medium and partly shielded from contact with water by the polar head groups. The hydrocarbon tails of the surfactant molecules, located in the interior of the micelle, interact with one another by weak van der Waals forces.

The size of a micelle or its aggregation number is governed largely by geometric factors. The radius of the hydrocarbon core cannot exceed the length of the extended hydrocarbon chain of the surfactant molecule. There, increasing the chain length or ascending homologous series increases the aggregation number of spherical micelles. If the surfactant concentration is increased beyond a few percent and if electrolytes are added (in the case of ionic surfactants) or the temperature is raised (in the case of nonionic surfactants), the micelles increase in size. Under these conditions, the micelles are too large to remain spherical and become ellipsoidal, cylindrical or finally lamellar in shape.

Common surfactants well known to one of skill in the art can be used in the micelles of the present disclosure. Suitable surfactants include sodium laureate, sodium oleate, sodium lauryl sulfate, octaoxyethylene glycol monododecyl ether, octoxynol 9 and PLURONIC® F-127 (BASF Corp., Florham Park, N.J.). Preferred surfactants are nonionic polyoxyethylene and polyoxypropylene detergents compatible with intravenous injection such as, TWEEN®-80, PLURONIC® F-68, n-octyl-beta-D-glucopyranoside, and the like. In addition, phospholipids, such as those described for use in the production of liposomes, may also be used for micelle formation.

In another preferred embodiment, the compounds disclosed herein are formulated as described in the literature for an administration route selected from: buccal delivery, sublingual delivery, transdermal delivery, inhalation and needle-free injection, such as using the methods developed by Powderjet.

For inhalation, the compounds disclosed herein can be formulated using methods known to those skilled in the art, for example an aerosol, dry powder or solubilized such as in microdroplets, preferably in a device intended for such delivery (such as commercially available from Aradigm Corp. (Hayward, Calif.), Alkermes, Inc. (Cambridge, Mass.), or Nektar Therapeutics (San Carlos, Calif.)).

Administration

Suitable dosing regimens for the various compounds and methods of the present disclosure are preferably determined taking into account factors well known in the art including, e.g., type of subject being dosed; age, weight, sex and medical condition of the subject; the route of administration; the renal and hepatic function of the subject; the desired effect; and the particular compound employed. Preferably, the composition will comprise about 0.5% to 75% by weight of a secretagogue disclosed herein, with the remainder consisting of suitable pharmaceutical excipients.

Optimal precision in achieving concentrations of drug within the range that yields efficacy without toxicity requires a regimen based on the kinetics of the drug's availability to target sites. This involves a consideration of the distribution, equilibrium, and elimination of a drug.

As described above, in one aspect, the secretagogue, such as ghrelin splice variant or a ghrelin splice variant-like compound, is administered subcutaneously.

In another aspect, the secretagogue, such as ghrelin splice variant or a ghrelin splice variant-like compound, is administered as a premeal bolus, wherein the administration form may be any suitable parenteral form. In a preferred embodiment, the secretagogue, such as ghrelin splice variant or a ghrelin splice variant-like compound, is administered subcutaneously in a premeal bolus.

The secretagogue, such as ghrelin splice variant or a ghrelin splice variant-like compound, can also be administered during a meal as a bolus. The mode of administration during a meal includes subcutaneous administration, such as a subcutaneously administered bolus.

Pharmaceutical compositions for parenteral administration include sterile aqueous and non-aqueous injectable solutions, dispersions, suspensions or emulsions, as well as sterile powders to be reconstituted in sterile injectable solutions or dispersions prior to use. Other suitable administration forms include suppositories, sprays, ointments, creams, gels, inhalants, dermal patches, implants, pills, tablets, lozenges and capsules.

A typical dosage is in a concentration equivalent to from 10 ng to 10 mg ghrelin splice variant per kg bodyweight. The concentrations and amounts herein are given in equivalents of amount ghrelin splice variant, wherein the ghrelin splice variant is a 22 amino acid human ghrelin splice variant (SEQ ID NO:2) and/or a 29 amino acid human ghrelin splice variant (SEQ ID NO:5) and/or a 24 amino acid human ghrelin splice variant (SEQ ID NO:3) and/or a 24 amino acid human ghrelin splice variant having a Dpr residue at the third position (SEQ ID NO:4). Equivalents may be tested as described in the section entitled "functionality", above.

In a preferred embodiment, the medicament is administered in a concentration equivalent to from 0.1 µg to 1 mg ghrelin splice variant per kg bodyweight such as from 0.5 µg to 0.5 mg ghrelin splice variant per kg bodyweight, such as from 1.0 µg to 0.1 mg ghrelin splice variant per kg bodyweight, such as from 1.0 µg to 50 µg ghrelin splice variant per kg bodyweight, such as from 1.0 µg to 10 µg ghrelin splice variant per kg bodyweight.

As described above, the secretagogue, such as ghrelin splice variant or a ghrelin splice variant-like compound, is preferably administered as a bolus. Accordingly, in one embodiment the medicament is administered as a bolus prior to a meal, said bolus comprising an amount of the secretagogue or a salt thereof equivalent to from 0.3 µg to 600 mg ghrelin splice variant. More preferably, the medicament is administered as a bolus prior to a meal, said bolus comprising an amount of the secretagogue or a salt thereof equivalent to from 2.0 µg to 200 mg ghrelin splice variant, such as from 5.0 µg to 100 mg ghrelin splice variant, such as from 10 µg to 50 mg ghrelin splice variant, such as from 10 µg to 5 mg ghrelin splice variant, such as from 10 µg to 1.0 mg ghrelin splice variant.

It should be noted that the normal ghrelin splice variant-like response which occurs before a meal is a short-lived surge in plasma concentrations of ghrelin splice variant and that, due to the relatively short half life of the peptide, an intravenous injection of ghrelin splice variant will ensure that a similar short-lived peak on ghrelin splice variant concentrations can be obtained. The administration route must ensure that the non-degraded, bioactive form of the peptide will be the dominating form in the circulation, which will reach and stimulate the ghrelin splice variant receptors.

Thus, in order to obtain the maximum effect of the medicament, it is preferably administered from one to three times daily, each administration being within 45 minutes of a meal, such as within 30 minutes of a meal, such as within 25 minutes of a meal, such as within 20 minutes of a meal, such as within 15 minutes of a meal, such as within 10 minutes of a meal, such as within 5 minutes of a meal. More preferably, the medicament is administered prior to each main meal, such as administered three times daily.

Compounds disclosed herein may also be formulated for nasal administration. The solutions or suspensions are applied directly to the nasal cavity by conventional means, for example with a dropper, pipette or spray. The compositions may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds disclosed herein may be formulated for aerosol administration, particularly to the respiratory tract and including intranasal administration. The compound will normally have a small particle size, for example of the order of 5 microns or less. Such a particle size may be obtained by means known in the art, for example by micronization. The active ingredient is provided in a pressurized pack with a suitable propellant such as a hydrofluoroalkane (HFA) for example hydrofluoroalkane-134a and hydrofluoroalkane-227, carbon dioxide or other suitable gas. The aerosol may conveniently also contain a surfactant such as lecithin. The dose of drug may be controlled by a metered valve. Alternatively, the active ingredients may be provided in a form of a dry powder, for example a powder mix of the compound in a suitable: powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of, e.g., gelatin or blister packs from which the powder may be administered by means of an inhaler.

Compositions administered by aerosols may be prepared, for example, as solutions in saline, employing benzyl alcohol or other suitable preservatives, absorption promoters to enhance bioavailability, employing fluorocarbons, and/or employing other solubilizing or dispersing agents.

Compounds disclosed herein may also be formulated for administration by injection pen in a similar way as for cartridged growth hormone (GH) or Insulin. The cartridge contains compounds disclosed herein in solvents. The pen, which is basically a needle, syringe and vial in one piece, is operated by a turning movement and allows different doses to be administrated. This device offers simplicity, convenience, and enhanced safety features for compounds delivery. It provides a simple device design, few administration steps and one-step dial-back dose knob. Such injection pen can be obtained by means known in art. For example, several manufacturers offer drug developers injection pens to be used with the drug developers compounds (BD—Medical-Pharmaceutical Systems, Inc.; Owen Mumford Inc. etc.).

Compositions for Oral Administration

Those secretagogue types capable of remaining biologically active in an individual after oral administration (such as, e.g., small molecules and short peptides) can be formulated in a wide range of oral administration dosage forms. The pharmaceutical compositions and dosage forms may comprise the compounds disclosed herein or their pharmaceutically acceptable salt or crystal forms thereof as the active component.

The pharmaceutical acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, wetting agents, tablet disintegrating agents, or an encapsulating material.

For oral administration, such excipients include, e.g., pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. The powders and tablets preferably containing from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include a composition comprising an active compound disclosed herein with encapsulating material as carrier providing a capsule in which the active component, with or without carriers, is surrounded by a carrier, which is in association with it. Similarly, cachets and lozenges are included.

Tablets, powders, capsules, pills, cachets, and lozenges can be as solid s suitable for oral administration.

Drops may comprise sterile or nonsterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Compositions for Parenteral Administration

The compounds disclosed herein may be formulated for parenteral administration (e.g., by injection, for example bolus injection or continuous infusion) and may be presented in unit dose form in ampules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water. Aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions of ghrelin splice variant or a ghrelin splice variant-like compound or pharmaceutical acceptable salt thereof (and for example antigenic epitopes and protease inhibitors) can be prepared in water or saline, and optionally mixed with a nontoxic surfactant. Compositions for intravenous or intra-arterial administration may include sterile aqueous solutions that may also contain buffers, liposomes, diluents and other suitable additives.

Oils useful in parenteral compositions include petroleum, animal, vegetable, or synthetic oils. Specific examples of oils useful in such compositions include peanut, soybean, sesame, cottonseed, corn, olive, petrolatum, and mineral. Suitable fatty acids for use in parenteral compositions include oleic acid, stearic acid, and isostearic acid. Ethyl oleate and isopropyl myristate are examples of suitable fatty acid esters.

Suitable soaps for use in parenteral compositions include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates; (c) nonionic detergents such as, for example, fatty amine oxides, fatty acid alkanolamides, and polyoxyethylenepolypropylene copolymers; (d) amphoteric detergents such as, for example, alkyl-beta-aminopropionates, and 2-alkyl-imidazoline quaternary ammonium salts; and (e) mixtures thereof.

The parenteral compositions typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such compositions will typically range from about 5 to about 15% by weight. Suitable surfactants include polyethylene sorbitan fatty acid esters, such as sorbitan monooleate and the high molecular weight adducts of ethylene oxide with a hydrophobic base, formed by tile condensation of propylene oxide with propylene glycol. The parenteral compositions can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The pharmaceutical dosage forms suitable for injection or infusion can include sterile aqueous solutions or dispersions comprising the active ingredient that are adapted for administration by encapsulation in liposomes. In all cases, the ultimate dosage form must be sterile, fluid and stable under the conditions of manufacture and storage.

Sterile injectable solutions are prepared by incorporating ghrelin splice variant or a ghrelin splice variant-like compound or pharmaceutical acceptable salt thereof in the required amount in the appropriate solvent with various of the other ingredients enumerated above, as required, followed by, e.g., filter sterilization.

Compositions for Topical Administration

The compounds disclosed herein can also be delivered topically. Regions for topical administration include the skin surface and also mucous membrane tissues of the rectum, nose, mouth, and throat. Compositions for topical administration via the skin and mucous membranes should not give rise to signs of irritation, such as swelling or redness.

The topical composition may include a pharmaceutical acceptable carrier adapted for topical administration. Thus, the composition may take the form of, for example, a suspension, solution, ointment, lotion, cream, foam, aerosol, spray, suppository, implant, inhalant, tablet, capsule, dry powder, syrup, balm or lozenge. Methods for preparing such compositions are well known in the pharmaceutical industry.

The compounds disclosed herein may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Compositions suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Creams, ointments or pastes according to the present disclosure are semi-solid compositions for external application comprising the active ingredient. They may be made by mixing the active ingredient in finely-divided or powdered form, alone or in solution or suspension in au aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives; or a fatty acid such as steric or oleic acid together with an alcohol such as propylene glycol or a macrogel. The composition may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present disclosure include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

The compounds described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the active compound to a patient's skin for an extended period of time. Transdermal patches have the added advantage of providing controlled delivery of a compound complex to the body (see Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987)). Such dosage forms can be made by dissolving, dispersing, or otherwise incorporating a compound disclosed herein in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

A variety of types of transdermal patches will find use in the methods described herein. For example, a simple adhesive patch can be prepared from a backing material and an acrylate adhesive. The active compound and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver a compound disclosed herein. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

A liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system (See U.S. Pat. Nos. 4,816,258; 4,927,408; 4,904,475; 4,588,580, 4,788,062; and the like, all of which are incorporated herein by reference). The rate of drug delivery will be dependent, in part, upon the nature of the membrane. For example, the rate of drug delivery across membranes within the body is generally higher than across dermal barriers. The rate at which the active compound is delivered from the device to the membrane is most advantageously controlled by the use of rate-limiting membranes which are placed between the reservoir and the skin. Assuming that the skin is sufficiently permeable to the active compound (i.e., absorption through the skin is greater than the rate of passage through the membrane), the membrane will serve to control the dosage rate experienced by the patient.

Suitable permeable membrane materials may be selected based on the desired degree of permeability, the nature of the active compound, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions disclosed herein may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

Compositions for Administration as Suppositories

The compounds disclosed herein may be formulated for administration as suppositories. A typical suppository is produced by providing a low melting wax, such as a mixture of fatty acid glycerides or cocoa butter, that is first melted and the active component is dispersed homogeneously therein, for example, by stirring. The molten homogeneous mixture is then poured into convenient sized molds, allowed to cool, and to solidify.

The active compound may be formulated into a suppository comprising, for example, about 0.5% to about 50% of a compound disclosed herein, disposed in a polyethylene glycol (PEG) carrier (e.g., PEG 1000 [96%] and PEG 4000 [4%]).

Formulation

A preferred aspect contemplates pharmaceutical compositions useful for practicing the therapeutic methods described herein. Pharmaceutical compositions can contain a physiologically tolerable carrier together with at least one species of a secretagogue, such as ghrelin splice variant or a ghrelin splice variant-like compound as described herein, dissolved or dispersed therein as an active ingredient. In a preferred embodiment, the pharmaceutical composition is not immunogenic when administered to a human individual for therapeutic purposes, unless that purpose is to induce an immune response.

One aspect relates to a pharmaceutical composition comprising at least one secretagogue, such as ghrelin splice variant or a ghrelin splice variant-like compound as defined above in Formula I. In a preferred embodiment, the pharmaceutical composition comprises at least two different ghrelin splice variant-like compounds as defined above in Formula i in order to increase the effect of the treatment. The difference may for example be compounds having different acylations as discussed above.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically, such compositions are prepared as sterile injectables either as liquid solutions or suspensions, aqueous or non-aqueous; however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. It is preferred that the formulation has a pH within the range of 3.5-8, such as in the range 4.5-7.5, such as in the range 5.5-7, such as in the range 6-7.5, most preferably around 7.3. However, as is understood by one skilled in the art, the pH range may be adjusted according to the individual treated and the administration procedure. For example, certain secretagogues, such as ghrelin splice, variant and ghrelin splice variant homologs, may be easily stabilized at a lower pH; so, in another preferred embodiment, the formulation has a pH within the range 3.5-7, such as 4-6, such as 5-6, such as 5.3-5.7, such as 5.5.

Pharmaceutical compositions disclosed herein can include pharmaceutically acceptable salts of the compounds therein. These salts will be ones which are acceptable in their application to a pharmaceutical use, meaning that the salt will retain the biological activity of the parent compound and the salt will not have untoward or deleterious effects in its application and use in treating diseases.

Pharmaceutically acceptable salts are prepared in a standard manner. If the parent compound is a base, it is treated with an excess of an organic or inorganic acid in a suitable solvent. If the parent compound is an acid, it is treated with an inorganic or organic base in a suitable solvent.

The compounds disclosed herein may be administered in the form of an alkali metal or earth alkali metal salt thereof, concurrently, simultaneously, or together with a pharmaceutically acceptable carrier or diluent, especially and preferably in the form of a pharmaceutical composition thereof, whether by, e.g., oral, rectal, or parenteral (including subcutaneous) route, in an effective amount.

Examples of pharmaceutical acceptable acid addition salts for use in the present inventive pharmaceutical composition include those derived from mineral acids, such as, e.g., hydrochloric, hydrobromic, phosphoric, metaphosphoric, nitric and sulfuric acids, and organic acids, such as, e.g., tartaric, acetic, citric, malic, lactic, fumaric, benzoic, glycolic, gluconic, succinic, p-toluenesulphonic, and arylsulphonic acids.

Other suitable pharmaceutically acceptable salts include the acid addition salts (formed with the free amino groups of the polypeptide). Other examples of salts include pharmaceutically acceptable acid addition salts, pharmaceutically acceptable metal salts, ammonium salts and alkylated ammonium salts. Acid addition salts include salts of inorganic acids as well as organic acids. Representative examples of suitable inorganic acids include hydrochloric, hydrobromic, hydriodic, phosphoric, sulfuric and nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmritic, ethylenediaminetetraacetic (EDTA), p-aminobenzoic, glutamic, benzenesulfonic, and p-toluenesulfonic acids and the like. Further examples of pharmaceutically acceptable inorganic or organic acid addition salts include the pharmaceutical acceptable salts listed in Berge S. M. et al., J. Pharm. Sci. 66:1-19 (1977), which is incorporated herein by reference. Examples of metal salts include lithium, sodium, potassium and magnesium salts and the like.

Examples of ammonium and alkylated ammonium salts include ammonium, methylammonium, dimethylammonium, trimethylammonium, ethylammonium, hydroxyethylammonium, diethylammonium, butylammonium and tetramethylammonium salts and the like.

Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Also included within the scope of compounds or pharmaceutical acceptable acid addition salts thereof in the context of the present disclosure are any hydrates (hydrated forms) thereof.

For parenteral administration, solutions of the present compounds in sterile aqueous solution, aqueous propylene glycol or sesame or peanut oil may be employed. Such aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

The pharmaceutical compositions formed by combining the compounds disclosed herein and the pharmaceutical acceptable carriers are then readily administered in a variety of dosage forms suitable for the disclosed routes of administration. The formulations may conveniently be presented in unit dosage form by methods known in the art of pharmacy.

In a preferred embodiment, the formulation comprises the secretagogue or a salt thereof as a lyophilisate, and the formulation further comprises a solvent, said lyophilisate and said solvent being in separate compartments until administration. In another embodiment, the formulation is a solution of the secretagogue or a salt thereof. In either embodiment, the solvent may be any suitable, such as those described herein, and preferably the solvent is saline.

Another aspect relates to a method for preparing a medicament or pharmaceutical composition comprising a compound disclosed herein, the method comprising admixing at least one ghrelin splice variant-like compound, as defined above in Formula I, with a physiologically acceptable carrier. A further aspect relates to a pharmaceutical composition comprising, as an active ingredient, a compound as defined above in Formula I or a pharmaceutically acceptable salt thereof together with a pharmaceutically-acceptable carrier. Accordingly, the formulation may further include the transport molecules as described above.

Combination Treatments

In a further aspect, the present compounds may be administered in combination with additional pharmacologically-active substances or other pharmacologically-active material and/or may be administered in combination with another therapeutic method. By the phrase "in combination with another substance(s) and/or therapeutic method(s)" is meant herein that said another substance(s) and/or therapeutic method(s) is administered to the individual thus treated before, during (including concurrently with) and/or after treatment of an individual with a secretagogue. In all cases of combination treatment described herein, the combination may be in the form of kit-in-part systems, wherein the combined active substances may be used for simultaneous, sequential or separate administration. In all cases, it is preferred that any of the herein-mentioned medicaments are administered in pharmaceutically effective amounts, i.e. an administration involving a total amount of each active component of the medicament or pharmaceutical composition or method that is sufficient to show a meaningful patient benefit.

In the following sections, combination therapies for use in preferred embodiments are grouped as follows:

1) Combinations wherein all active ingredients are appetite-regulating agents or in other ways useful for treating neuronal damage and/or neurodegenerative disease.

The secretagogue(s) according to the present disclosure can be administered in combination with other appetite-regulating agents, including more than one type of growth hormone secretagogue, such as another ghrelin splice variant-like compound, such as a ghrelin splice variant-like compound comprising a structure defined by Formula I, described herein. Other secretagogues suitable for combination administration with another secretagogue compound are any of the secretagogue compounds described herein. In one preferred embodiment, ghrelin splice variant (most preferably human ghrelin splice variant) is administered in combination with a different, ghrelin splice variant-like compound—this combination is envisaged to enhance and/or prolong the effect of the secretagogues on the ghrelin receptor. In a similar way, several different secretagogues may be administered to an individual to increase efficacy on the ghrelin receptor, such as greater than 2 different secretagogue types, such as 3, such as 4, such as 5, such as 6, such as 7, such as greater than 8 different secretagogue types. The secretagogue according to the present disclosure, such as ghrelin splice variant or a ghrelin splice variant-like compound(s) can also be administered in combination with a pharmaceutically effective amount of a growth hormone, including hGH.

In one preferred embodiment, the secretagogue, such as ghrelin splice variant or a ghrelin splice variant-like compound, may be administered in combination with IGF-1, IGFBP-3, or ALP, preferably with IGF-1. The rationale behind this combination treatment is to increase the level of IGF-1, IGFBP-3, and/or ALP found to be low in cachectic individuals.

In a further embodiment, the secretagogues, such as ghrelin splice variant or a ghrelin splice variant-like compound, may be administered in combination with compounds known to stimulate appetite, such as ghrelin, melanocortin receptor antagonists, neuropeptide Y receptor agonists including agonists selective for individual subtypes of the neuropeptide Y receptors, leptin or leptin receptor agonists, cannabinoids including marijuana and marijuana derivatives, antipsychotics, especially atypical antipsychotics such as sertindole, Sufpirid, Clozapine, Risperidone, Quetiapin, Amisulpride, Ziprasidon, and Olanzapine.

2) Combinations of the secretagogue, such as ghrelin splice variant or a ghrelin splice variant-like compound, with an ingredient or therapy active against a disease causing or being associated with the disease or condition treated with the secretagogue, such as ghrelin splice variant or a ghrelin splice variant-like compound.

Particularly in relation to neuronal damage and/or neurodegenerative disease, administration of a secretagogue, such as a ghrelin splice variant-like compound, may be performed in combination with any anti-neurodegenerative or supportive therapy, including levodopa and/or dopamine agonist therapy and surgical treatment. In particular, it is used in combination with levodopa and dopamine agonist therapy. Thus, one embodiment relates to a method of treating cancer comprising administering an effective amount of dopamine agonist therapy and an effective amount of a secretagogue, such as a ghrelin splice variant-like compound according to the present disclosure. The treatment with the secretagogue, such as a ghrelin splice variant-like compound, may be started before the levodopa and/or dopamine agonist therapy treatment initiates. It may be administered continuously during the levodopa and/or dopamine agonist therapy or it may be administered at intervals, for example between periods with radiotherapy therapy.

Another embodiment relates to a method of treating neurodegenerative disease comprising administering an effective amount of levodopa and/or dopamine agonist therapy and an effective amount of a secretagogue, such as a ghrelin splice variant-like compound according to the present disclosure. The treatment with the secretagogue, such as a ghrelin splice variant-like compound, may be started before the levodopa and/or dopamine agonist therapy treatment initiates. It may be administered continuously during the levodopa and/or dopamine agonist therapy, or it may be administered at intervals, for example between periods with levodopa and/or dopamine agonist therapy.

Furthermore, the combination treatment may be co-formulations of the secretagogue, such as a ghrelin splice variant-like compound, and the anti neurodegenerative therapy.

A secretagogue according to the present disclosure, such as ghrelin splice variant or a ghrelin splice variant-like compound, may also be administered in combination with a pharmaceutically effective amount of glucocorticoid steroids and prokinetic treatment as well as other treatment used in cancer therapy. Thus, in another preferred embodiment, a secretagogue according to the present disclosure, such as ghrelin splice variant or a ghrelin splice variant-like compound, is administered in combination with a pharmaceutical effective amount of one or more of: progestational drugs, such as megastrol and/or cyproheptadines (and/or other 5-HT receptor antagonists); and/or branched chain amino acids; and/or oxandralin; and/or anti-TNF-α agents, such as infliximab, etanercept, or adalimumab; and/or testosterone; and/or a "cocktail" comprising immunonutrition drugs, antioxidants and COX2 inhibitors; and/or cannabinoids; and/or eicosapentaenoic acid; and/or melatonin; and/or thalidomide; and/or a β2 adrenergic drug; most preferably for the treatment of neurodegenerative disease, such as parkinson's disease or alzheimers disease.

In yet another embodiment, the secretagogue, such as a ghrelin splice variant-like compound, is administered in combination with anti-inflammatory compounds, preferably an NSAID, such as indomethacin, and COX1 inhibitors or COX2 inhibitors; and/or anti-TNF-α compounds such as infliximab, etanercept, or adalimumab. Another combination may be with erythropoietin/EPO. Another combination can be with angiotensin II lowering agents, such as Vitor. Another combination can be with selective androgen receptor modulator(s). Another combination may be with one or more of leptin, agonists of the renin-angiotensin system, opioid receptor agonists or peroxisome proliferator-activated receptor gamma agonists.

In relation to treatment of lipodystrophy, another embodiment relates to a treatment wherein a secretagogue, such as ghrelin splice variant, more preferably a ghrelin splice variant-like compound, is administered in combination with a lipodystrophy treatment, such as one or more of the treatments or compounds described herein suitable for treating a lipodystrophic syndrome.

Thus, other pharmacologically active substances that may be administered in combination with said secretagogue, such as a ghrelin splice variant-like compound, in the methods of the present disclosure comprise:

(a) Leptin: Leptin has been shown to have a positive effect on the metabolic abnormalities associated with lipodystrophy (Oral E. A. et al., J. Clin. Endocrinol. Metab. 91:621-28 (2006)). This treatment has proven to be beneficial both to those patients that suffer from a low plasma level of leptin and to those that have a normal level.

(b) Peroxisome proliferator-activated receptor (PPAR-γ) agonists: PPAR-γ has in several studies been demonstrated to be important for adipocyte metabolism and metabolic syndrome, and it is proposed that PPAR-γ agonists will decrease the symptoms of lipodystrophy (Semple R. K. et al., J. Clin. Invest 116:581-89 (2006)).

(c) Agonists of the renin-angiotensin system: It has been shown that treatment with HAART increases the activity of ACE in the T-cells, which means that agonists of the renin-angiotensin system may improve HAART induced lipodystrophy (Hegele R. A. & Leff T., J. Clin. Invest. 114:163-65 (2004)).

(d) Opioid receptor antagonists: Opioid receptor antagonists, such as Naloxone and Naltrexone, have been shown to prolong the period of time from protease inhibitor treatment to development of the first symptoms of lipodystrophy (AIDS Patient Care STDS 14:283 (2000)).
(e) Des-acyl ghrelin splice variant: Ghrelin splice variant in combination with des-acyl ghrelin splice variant has been found to decrease insulin resistance, which is an important feature of the lipodystrophy syndrome (Koutkia P. et al., Am. J. Physical. Endocrinol. Metab. 286:E296-303 (2004)).
(f) Adiponectin and anti-diabetic treatment including other compounds for the treatment and/or prevention of insulin resistance and diseases wherein insulin resistance is the pathophysiological mechanism.
(g) Therapy with rhGH has been reported to cause reduction in the size of "buffalo hump", truncal fat and to increase the lean body mass in a small number of patients (Lo J. C. et al., J. Clin. Endocrinol. Metab. 86:3480-87 (2001)). However, fat loss and lipid abnormalities did not improve and blood glucose control worsened. Examples of syndromes treated with hGH include HIV, AIDS and cancer. Without being bound by theory, it is believed that treatment with ghrelin splice variant or a analog thereof would maintain and/or increase body fat in patients being treated with hGH, thereby effectively counteracting or at least reducing lipodystrophy caused by hGH. Thus, one preferred embodiment relates to use of ghrelin splice variant or ghrelin splice variant-like compound in combination with a growth hormone, preferably in individuals suffering from neurodegenerative disease. Said treatment with ghrelin splice variant or an analog thereof may be prior to, and/or during and/or after the individual is subjected to treatment with a growth hormone. Said growth hormone is preferably hGH.
(h) Treatment with combinations of different secretagogues as described above under group 1), supra.

3) Combinations of the secretagogue, such as ghrelin splice variant or a ghrelin splice variant-like compound, with an ingredient active or therapy against symptoms associated with the disease or condition treated with the secretagogue, such as ghrelin splice variant or a ghrelin splice variant-like compound.

One aspect relates to combination treatment, wherein one of the ingredients in the combination is used for treating symptoms or conditions that may be encountered in individuals suffering from neuronal damage and/or neurodegenerative disease. Thus, uses and combination treatments involving administration of a secretagogue, such as the ghrelin splice variant-like compound according to the present disclosure, can also involve treatment in combination with one or more of
a) prophylaxis and/or alleviation and/or treatment of a clinical depression, which combination treatment further comprises administering an antidepressant, a prodrug thereof, or a pharmaceutical acceptable salt of said antidepressant or said prodrug. In the above combination treatment, the antidepressant is preferably a norepinephrine reuptake inhibitor (NERI), a selective serotonin reuptake inhibitor (SSRI), a monoamine oxidase inhibitor (MAO), a combined NERI/SSRI, or an atypical antidepressant, a prodrug of said antidepressant or a pharmaceutically acceptable salt of said antidepressant or said prodrug. Preferred antidepressants are SSRI, a prodrug thereof or a pharmaceutical acceptable salt of said SSRI or said prodrug. The SSRI is preferably citalopram, esciraloprain, femoxetine fluoxetine, fluvoxamine, indalpine, indeloxazine, milnacipran, paroxetine, sertraline, sibutramine or zimeldine, prodrug of said SSRI or a pharmaceutical acceptable salt of said SSRI or said prodrug. Of the above, citalopram and escitalopram, a prodrug or a pharmaceutical acceptable salt thereof, are preferred in certain embodiments of combination treatments.
b) prophylaxis and/or alleviation and/or treatment of an emetic condition, including nausea and vomiting, which combination treatment further comprises administering an antiemetic agent, a prodrug thereof, or a pharmaceutically acceptable salt of said antiemetic agent or said prodrug. Preferred antiemetic agents used in combination treatments according to the present disclosure include meclizine hydrochloride, prochlorperazine, promethazine, trimethobenzamide hydrochloride and ondansetron hydrochloride. In particular, emesis may be caused by cancer, either due to the anti-cancer treatment or due to the cancer disease as such.
c) prophylaxis and/or alleviation and/or treatment of a psychotic condition, which combination treatment further comprises administering an antipsychotic agent, a prodrug thereof or a pharmaceutical acceptable salt of said antipsychotic agent or said prodrug. Preferred antipsychotic agents used in combination treatments in accordance with the present disclosure include chlorpromazine, haloperidol, clozapine, loxapine, molindone hydrochloride, thiothixene, olanzapine, ziprasidone, ziprasidone hydrochloride, prochlorperazine, perphenazine, trifluoperazine hydrochloride and risperidone.
d) prophylaxis and/or alleviation and/or treatment of anxiety, which combination treatment further comprises administering an antianxiety agent, a prodrug thereof or a pharmaceutically acceptable salt of said antianxiety agent or said prodrug. Preferred antianxiety agents used in combination treatments in accordance with the present disclosure include alprazolam, clonazepam, lorazepam, oxazepam, chlordiazepoxide hydrochloride, diazepam, buspirone hydrochloride, doxepin hydrochloride, hydroxyzine pamoate and clonazepam.

Of course, combinations of the above groups (1-3) are also within the scope of this disclosure.

Medical Packaging

The compounds disclosed herein may be administered alone or in combination with pharmaceutically acceptable carriers or excipients, in either single or multiple doses.

The formulations may conveniently be presented in unit dosage form by methods known to those skilled in the art.

It is preferred that the compounds according to the present disclosure are provided in a kit. Such a kit typically contains an active compound in dosage forms for administration. A dosage form contains a sufficient amount of active compound such that a desirable effect can be obtained when administered to a subject, preferably prior to at least one meal a day, more preferably prior to each main meal, such as three times a day, during the course of 1 or more days. Thus, it is preferred that the medical packaging comprises an amount of dosage units corresponding to the relevant dosage regimen. Accordingly, in one embodiment, the medical packaging comprises a pharmaceutical composition comprising a compound as defined above or a pharmaceutically acceptable salt thereof and pharmaceutically acceptable carriers, vehicles and/or excipients, said packaging having from 7 to 21 dosage units, or multiple thereof, thereby having dosage units tier one week of administration or several weeks of administration.

In one embodiment, the medical, packaging is for administration once daily in a week, and comprises 7 dosage units, in another embodiment the medical packaging is for administration twice daily, and comprises 14 dosage units. In yet another more preferred embodiment, the medical packaging is for administration three times daily, and comprises 21 dosage units.

The dosage units are as defined above, i.e. a dosage unit preferably comprises an amount of the ghrelin splice variant-like compound or a salt thereof equivalent to from 0.3 µg to 600 mg ghrelin splice variant, such as of from 2.0 µg to 200 mg ghrelin splice variant, such as from 5.0 µg to 100 mg ghrelin splice variant, such as from 10 µg to 50 mg ghrelin splice variant, such as from 10 µg to 5 mg ghrelin splice variant, such as from 10 µg to 1.0 mg ghrelin splice variant.

The medical packaging may be in any suitable form for parenteral, in particular subcutaneous, administration. In a preferred embodiment, the packaging is in the form of a cartridge, such as a cartridge for an injection pen, the injection pen being such as an injection pen known from insulin treatment or from hGH treatment.

When the medical packaging comprises more than one dosage unit, it is preferred that the medical packaging is provided with a mechanism to adjust each administration to one dosage unit only.

Preferably, a kit contains instructions indicating the use of the dosage form to achieve a desirable affect and the amount of dosage form to be taken over a specified time period. Accordingly, in one embodiment the medical packaging comprises instructions for administering the pharmaceutical composition. In particular said instructions may include instructions referring to administration of said pharmaceutical composition either during a meal, or preferably at the most 45 minutes prior to a meal, such as at the most 30 minutes prior to a meal, such as at the most 25 minutes prior to a meal, such as at the most 20 minutes prior to a meal, such as at the most 15 minutes prior to a meal, such as at the most 10 minutes prior to a meal, such as at the most 5 minutes prior to a meal.

Method for Monitoring the Effect of Treatment with Ghrelin Splice Variant and/or a Ghrelin Splice Variant-Like Compound Another aspect relates to a method for monitoring the effect of the administration of a secretagogue, such as the ghrelin splice variant-like compounds disclosed herein, in a method of the present disclosure, comprising measuring one or more markers, in particular markers, selected from GH, IGF-1, IGFBP-3, ALP (acidic labeled), thyroid hormones, sex hormones, and albumin; more preferably selected from IGF-1, IGFBP-3, ALP (acidic labeled); even more preferably IGF-1. These markers are all low in cachetic patients and are expected to increase after treatment with ghrelin splice variant. Other markers that are expected to increase after treatment with ghrelin splice variant are the blood GH level and the body weight. In addition, the body composition is expected to change, and the lean body mass is expected to increase. The body composition changes can be assessed by using MRI or NMR.

Thus, one embodiment relates to a method for monitoring the effect of any of the treatments of an individual with a secretagogue described herein, said method comprising measuring the blood level of said individual of one or more of: (i) IGF-1 and/or (ii) IGFBP-3 and/or (iii) ALP and/or (iv) one or more thyroid hormones and/or (v) one or more sex hormones and/or (vi) albumin or, more preferably, one or more of: (i) IGF-1 and/or (ii) IGFBP-3 and/or (iii) ALP and/or (iv) GH and/or (v) body weight and/or (vi) body composition.

Methods for measuring substances in the blood level of an individual are well known hi the art. As an example, an isolated blood sample may be tested by methods such as Western blot or by enzyme-linked assay (ELISA).

EXAMPLES

The present disclosure is further defined in the following Examples. It should be understood that these Examples, while indicating preferred embodiments, are given by way of illustration only. From the above discussion and these Examples, one skilled in the art can ascertain the preferred features of this disclosure, and without departing from the spirit and scope thereof, can make various changes and modifications to adapt it to various uses and conditions.

Examples 2, 5, 7, 8, and 9 are working examples. Examples 1, 3, 4, 10, and 11 are prophetic examples.

Example 1

Competition Binding Assays

Transfected COS-7 cells are transferred to culture plates one day after transfection at a density of $1\times10^5$ cells per well aiming at 5-8% binding of the radioactive ligand. Two days after transfection, competition binding experiments are performed for 3 hours at 4° C. using 25 pM of $[^{125}I]$Ghrelin (GE Healthcare, Piscataway, N.J., USA). Binding assays are performed in 0.5 ml of a 50 mM Hepes buffer, pH 7.4, supplemented with 1 mM $CaCl_2$, 5 mM $MgCl_2$, and 0.1% (w/v) bovine serum albumin, 40 µg/ml bacitracin. Non-specific binding is determined as the binding in the presence of 1 micromole of unlabeled Olefin splice variant. Cells are washed twice in 0.5 ml of ice-cold buffer and 0.5-1 ml of lysis buffer (8 M Urea, 2% NP40 in 3 M acetic acid) is added and the bound radioactivity is counted. Determinations are made in duplicate.

Example 2

Synthetic Production of Ghrelin Splice Variant-Like Compound

Amino acid derivatives and synthesis reagents can be obtained from commercial sources. Peptide chain extension can be performed using Applied Biosystem 433A synthesizer produced by Perkin Elmer, and a protected peptide derivative-resin can be constructed by the Boc or Fmoc method. The protected peptide resin obtained by the Boo method is deprotected with anhydrous hydrogen fluoride (HF) in the presence of p-cresol thereby releasing the peptide, which is then purified. The protected peptide resin obtained by the Fmoc method is deprotected with trifluoroacetic acid (TPA) or dilute TFA containing various scavengers, and the released peptide is purified. Purification is performed in reversed phase HPLC on a C4 or C18 column. The purity of the purified product can be confirmed by reverse phase HPLC, and its structure can be confirmed by amino acid composition analysis and mass spectrometry.

Peptides disclosed herein can be produced by a conventional peptide synthesis method. Specifically, synthesis of acylated or alkylated peptides is exemplified below.

Abbreviations: "HMP resin" means 4-hydroxymethylphenoxymethyl resin; "Fmoc amide resin" means 4-(2',4'-dimethoxyphenyl-Fmoc-aminomethyl) phenoxyacetamidoethyl resin; "PAM resin" means phenylacetoamidomethyl resin; "HBTU" means 2-(1H-benzotriazole-1-yl)-1,1,3,3-tetramethyluronium hexafluorophosphate; "TBTU" means 2-(1H-benzotriazole-1-yl)-1,1,3,3-tetramethyluronium tetrafluoroborate; "HOBt" means 1-hydroxybenzotriazole; "DCC" means dicyclohexylcarbodiimide; "DIPCI" means diisopropylcarbodiimide; "TFA" means trifluoroacetic acid; "DIPEA" means diisopropylethylamine; "TIPS" means triisopropylsilane; "Fmoc" means fluorenylmethoxycarbonyl; "Boc" means t-butyloxycarbonyi; "Trt" means trityl; "Bu" means t-butyl; "Pmc" means 2,2,5,7,8-pentamethylchroman-6-sulfonyl; "Prl" means propionyl; "PhPrl" means phenylpropionyl; "Bzl" means benzyl; "Bom" means benzyloxymethyl; "Tos" means toluenesulfonyl; "CI-Z" means 2-chloro-benzyloxycarbonyl; "Pis" means 2-phenylisopropyl; "Mtt" means 4-methyltrityl; "DMF" means N,N-dimethylformamide; "NMP" means N-methylpyrrolidone; "DMAP" means 4-dimethylaminopyridine; "HOSu" means N-hydroxysucciniimide; "Adod" means 2-aminododecanoic acid; "Aib" means 2-aminoisobutylic acid; "Ape" means 5-aminopentanoic acid; "Cha" means cyclohexylalanine; "Dap" means 2,3-diaminopropionic acid; "Nal" means naphtylalanine; "Nle" means norleucine.

Protecting amino acids which can be used in synthesis Fmoc method: Boc-Gly, Fmoc-Gly, Fmoc-Ser (Bu), Fmoc-Ser (Trt), Fmoc-Glu (OBu), Fmoc-His (Boc), Fmoc-Gln (Trt), Fmoc-Arg (Pmc), Fmoc-Lys (Boc), Fmoc-Pro, Fmoc-Leu, Fmoc-Ala, Fmoc-Val, Fmoc-Phe, Fmoc-Phe, Fmoc-Ser ($n$-$C_8H_{17}$), Fmoc-Ser ($n$-$C_8H_{17}$), Fmoc-Cys ($n$-$C_8H_{17}$), Fmoc-Asp (OPis), Fmoc-Ser (BzI), Fmoc-Cys (Trt), Fmoc-Dap (Octanoyl), Fmoc-2-Nal, Fmoc-2-Nal, Fmoc-Nle, Fmoc-Lys (Mtt), Fmoc-Aib-OH, Fmoc-Asp (O—$C_7H_{15}$). Boc method: Boc-Gly, Boc-Ser (Bzl), Boc-Ser (Ac), Boc-Ser (PrI), Boc-Glu (OBzl), Boc-His (Bom), Boc-Gln, Boc-Arg (Tos), Boc-Lys (CI-Z), Boc-Pro, Boc-Leu, Boc-Ala, Boc-Val, Boc-Phe, Boc-Cys ($n$-$C_8H_{17}$), Boc-Apc, Boc-Ser ($n$-$C_8H_{17}$)

Units used:
(a) Analytical HPLC system Unit: Shimadzu LC-10A System; Column: YMC PROTEIN-RP (4.6 mm×150 mm); Column temperature: 40° C.; Eluent: A linear gradient of from 0 to 50% acetonitrile for 20 minutes in 0.1% trifluoroacetic acid; Flow rate: 1 mL/min; Detection: UV (210 nm); Injection volume: 10 to 100 mu I.
(b) Preparative ITPLC system Unit: Waters 600 Multisolvent Delivery System; Columns: YMC-Pack-ODS-A (5 mm, 20 mm×250 mm) YMC-Pack-PROTEIN-RP (5 mu m, C4, 10 mm×250 mm) YMC-Pack PROTEIN-RP (5 mu m, C4, 20 mm×250 mm) YMC PROTEIN-RP (4.6 mm×150 mm); Eluent: A suitable linear gradient of acetonitrile concentration in 0.1% trifluoroacetic acid; Flow rate: 10 mL/min. (for columns of an inner diameter of 20 mm), 3 mL/min. (for the column of an inner diameter of 10 mm), 1 mL/min. (for the column of an inner diameter of 4.6 mm); Detection: 210 nm, 260 nm; injection: 10 to 2000 mu I (2000 mu I or more was injected via a pump)
(c) Mass spectrometer Unit: Finnigan MAT TSQ700; Ion source: ESI; Detection ion mode: Positive Spray; Voltage: 4.5 kV; Capillary temperature: 250° C.; Mobile phase: A mixture of 0.2% acetic acid and methanol (1:1); Flow rate: 0.2 mL/min; Scan range: 300 to 1,500
(d) Analysis of amino acid sequence Unit: Applied Biosystem 477A, 492 model sequencer manufactured by Perkin Elmer
(e) Analysis of amino acid composition Unit: L-8500 model amino acid analyzer manufactured by Hitachi, Co., Ltd.; Sample: Unless otherwise specified, the sample is hydrolyzed with 6 M HCl at 110° C. for 24 hours in a sealed tube.

Example of Synthesis of a Derivative Having Acyl Serine (Fmoc Method, Carboxyl-Terminal Amide Derivative) Ghrelin Splice Variant GSS (CO—$C_7H_{15}$) FLSPEHQRNQVRPPHKAPH Fmoc-His (Pmc)-HMP-resin (403 mg, 0.25 mmol, ABI Co., Ltd.) is treated with 20% piperazine for 20 minutes and subjected repeatedly to introduction of Fmoc-amino acid by HBTU/HOBt and elimination of Fmoc by piperazine sequentially to construct Fmoc-Ser (Bu)-Ser (Trt)-Phe-Leu-Ser (tBu)-Pro-Glu (OBu)-His (Boc)-Gln (Trt)-Arg (Pmc)-Val-Gln-Val (Trt)-Arg (Pmc)-Pro-Pro-His (Boc)-Lys (Boc)-Ala (Boc)-Pro (Boc)-Pro-His (Pmc)-resin. After Boc-Gly is finally introduced by DCC/HOBt, the resulting protected peptide resin (1.3 g) is treated with 1% TFA-5% TIPS-methylene chloride solution (15 mL) for 30 minutes.

The peptide resin is filtrated, washed several times with methylene chloride (30 mL), and washed with 5% DI EA (10 mL) and then with methylene chloride (30 mL). The resulting de-Trt peptide resin (about 1.3 g) is swollen with NMP (10 mL), and octanoic acid (144.2 mg, 1.0 mmol) and DIPCI (126.2 mg, 1.0 mmol) are added thereto in the presence of DMAP (61.1 mg, 0.5 mmol) and allowed to react for 8 hours. The resin is recovered by filtration and washed with NMP and then with methylene chloride, followed by drying under vacuum to give about 1.2 g protected peptide resin wherein the side chain of third serine is octanoylated. To this product is added a de-protecting reagent (10 mL) consisting of 88% TFA-5% phenol-2% TIPS-5% $H_2O$, and the mixture is stirred at room temperature for 2 hours. The resin is removed by filtration, and the filtrate is concentrated followed by adding ether to the resulting residues to form precipitates. The precipitates are recovered by filtration and dried to give about 550 mg crude peptide. 200 mg of this product is dissolved in 10 mL water and applied to YMC-Pack PROTEIN-RP (C4, 20 mm×250 mm) and eluted with a linear gradient (flow rate: 10 mL/min.) for 60 minutes of from 0 to 54% acetonitrile in 0.1% trifluoroacetic acid. The desired fractions are collected and lyophilized to give about 120 mg of the desired product.

Example of Synthesis of a Derivative Having Acyl Serine (Fmoc Method Carboxyl-Terminal Amide Compounds) Ghrelin Splice Variant (1-22)-$NH_2$ GSS (CO—$C_7H_{15}$) FLSPEHQRVQVRPPHKAPH-$NH_2$Fmoc-amide-resin (403 mg, 0.25 mmol, ABI Co., Ltd.) is treated with 20% piperazine for 20 minutes and subjected repeatedly to introduction of Fmoc-amino acid by HBTU/HOBt and elimination of Fmoc by piperazine sequentially to construct Fmoc-Ser (Bu)-Ser (Trt)-Phe-Leu-Ser (Bu)-Pro-Glu (OBu)-His (Boc)-Gln (Trt)-Arg (Pmc)-Val-Gln-Val (Trt)-Arg (Pmc)-Pro-Pro-His (Boc)-Lys (Boc)-Ala (Boc)-Pro (Boc)-Pro-His (Boc)-resin. After Boc-Gly is finally introduced by DCC/HOBt, the resulting protected peptide resin (about 550 mg) is treated with 1% TFA-5% TIPS-methylene chloride solution (10 mL) for 30 minutes. The peptide resin is recovered by filtration, washed several times with methylene chloride (30 mL), and washed with 5% DIEA (10 mL) and then with methylene chloride (30 mL). The resulting de-Trt peptide resin (about 750 mg) is swollen with NMP (10 mL), and octanoic acid (144.2 mg, 1.0 mmol) and DIPCI (126.2 mg, 1 mmol) are added thereto in the presence of DMAP (61.1 mg. 0.5 mmol) and allowed to react for 4 hours. The resin is recovered by filtration and washed with NMP and then with methylene chloride, followed by drying under vacuum to give about 800 mg protected peptide resin wherein the side chain of third serine is octanoylated. TFA (10 mL) is added to this product and stirred at room temperature for 30 minutes. The resin is removed by filtration, and the filtrate is then concentrated followed by adding ether to the resulting residues to form precipitates. The precipitates are recovered by filtration and dried to give about 250 mg crude peptide. About 200 mg of this product is dissolved in 10 mL of 30% aqueous acetic acid and applied to YMC-Pack PROTEIN-RP (C4, 20 mm×250 mm) and eluted with a linear gradient (flow rate: 10 mL/min.) for 60 minutes of from 0 to 54% acetonitrile in 0.1% trifluoroacetic acid. The desired fractions are collected and then lyophilized to give about 150 mg of the desired product.

Example of Synthesis of a Derivative Having Acyl Serine (Boc Method) [Ser3 (Propionyl)]-Ghrelin Splice Variant (1-22)

GSS (CO—CH$_2$CH$_3$) FLSPEHQRVQVRPPHKAPH protected ghrelin splice variant resin (4-22) is constructed from Boc-His (Tos)-Pam resin (0.75 g, 0.5 mmol) by Boc chemistry, and Boc-Ser (CO—CH$_2$CH$_3$)—OH, Boc-Ser (Bzl)-OH and Boc-Gly-OH are condensed with a half (1.4 g) of the resin. The resulting resin, 1.5 g, is then treated with a mixture of HF and p-cresol (8.5 mL:1.5 mL) at 0° C. for 1 hour, and the HF is evaporated. Ether is added to the residues, whereby 671 mg crude peptide is obtained. This sample is then dissolved in 50% acetic acid (AcOH) and applied to a preparative column YMC-Pack-ODS-A (5 mu m, 20 mm×250 mm) and eluted at a rate of 10 mL/min by a gradient of from 0 to 95% acetonitrile concentration in 0.1% TFA solution for 75 minutes. Those fractions containing the desired product are lyophilized to give approximately 135.8 mg crude peptide. A part (0.5 mg) of this product is applied to YMC-A-302 column (C18, 4.6 mm×150 mm) and eluted at a flow rate of 1 mL/min. by a gradient of from 15 to 19% concentration acetonitrile. This purification procedure is then repeated and the desired fractions are combined to give approximately 0.41 mg of the desired product.

Other compounds according to the present disclosure can be produced likewise.

The above method was used to synthesize acylated and non-acylated SEQ ID NO:2, SEQ ID NO:4, and SEQ ID NO:5.

Example 3

A Randomized, Single Center, Four-Period Crossover Trial to Investigate the Absolute Bioavailability of Intravenously Administered Ghrelin Splice Variant and Subcutaneously Administered Ghrelin Splice Variant at Three Different Single Doses in Healthy Subjects Objectives:
Primary: To investigate the absolute bioavailability of three different doses of ghrelin splice variant administered as single intravenous and subcutaneous closes.
Secondary:
1) To investigate the dose linearity (dose proportionality) of the ascending doses.
2) To investigate and compare the pharmacodynamic profiles between the treatments.
3) To assess the safety and local tolerability.
Trial Design: A randomized, single center, unbalanced block design, four-period crossover trial to investigate the absolute bioavailability between intravenously administered ghrelin splice variant and subcutaneously administered ghrelin splice variant at three different single doses in healthy subjects. Three doses will be used for each way of administration: low, medium and high. To reduce the number of dosings to each individual and hence reduce the length of the trial, each subject will only receive four doses of the total of six doses, i.e. two dose levels administered as intravenous and subcutaneous, respectively. The unbalanced block design will ensure that all three-dose levels will be covered in this way although not all subjects will receive all dose levels. A sufficient washout period will be placed between the individual dosing periods.
Endpoints:
Pharmacokinetics of ghrelin splice variant: $AUC_{0-t}$, AUC, $C_{max}$, $t_{max}$, t, $C_{1/f}$, $V_{z/f}$, $C_l$, $V_z$, $t_{1/z}$
MET Pharmacodynamics: GH: AUC, $C_{max}$ and $t_{max}$ Cardiac output, assessment of hunger, food/energy intake, degree of pleasure related to food intake, body mass, energy expenditure, DEXA.
Safety: Safety and local tolerability will be assessed throughout the study by clinical evaluations (physical examination and vital signs), electrocardiography and laboratory tests (hematology and clinical chemistry).
Trial population and power calculation: Healthy male subjects, aged 18-45 years with a body mass index (BMI) of 19-26 kg/m$^2$ (both inclusive).
The primary objective of this study is to investigate the absolute bioavailability of ghrelin splice variant administered via intravenous and subcutaneous administration. An unbalanced block design will be applied to reduce the trial period time and reduce the number of dosings per subject. The number of subjects needed to perform a statistical analysis of absolute bioavailability per dose levels as well as an analysis of dose linearity between doses will be calculated based on existing literature data.
Trial products: ghrelin splice variant for intravenous and subcutaneous administration.

Example 4

Functional Tests on the Ghrelin Receptor

Transfections and tissue culture-COS-7 cells are grown in Dulbecco's modified Eagle's medium 1885 supplemented with 10% fetal calf serum, 2 mM glutamine and 0.01 mg/ml gentamicin. Cells are transfected using calcium phosphate precipitation method with chloroquine addition as previously described (Hoist B. et al., Mol. Pharmacol. 53:166-175 (1998)). For gene dose experiments, variable amounts of DNA are used. The amount of cDNA (20 µg/75 cm$^2$) resulting in maximal signaling is used for dose response curves. HEK-293 cells are grown in D-MEM, Dulbecco's modified Eagle's medium 31966 with high glucose supplemented with 10% fetal calf serum, 2 mM glutamine and 0.01 mg/ml gentamicin. Cells are transfected with Lipofectamine™ 2000 (Invitrogen Corp., Carlsbad, Calif.).

Phosphatidylinositol turnover: One day after transfection, COS-7 cells are incubated for 24 hours with 5 µCi of [3H]-myo-inositol (GE Healthcare, Piscataway, N.J.) in 1 ml medium supplemented with 10% fetal calf serum, 2 mM glutamine and 0.01 mg/ml gentamicin per well. Cells are washed twice in buffer, 20 mM HEPES, pH 7.4, supplemented with 140 mM NaCl, 5 mM KCl, 1 mM MgSO$_4$, 1 mM CaCl$_2$, 10 mM glucose, 0.05% (w/v) bovine serum; and are incubated in 0.5 ml buffer supplemented with 10 mM LiCl at 37° C. for 30 min. After stimulation with various concentrations of peptide for 45 min at 37° C., cells are extracted with 10% ice-cold perchloric acid followed by incubation on ice for 30 min. The resulting supernatants are neutralized with KOH in HEPES buffer, and the generated [3H]-inositol phosphate is purified on Bio-Rad AG 1-X8 anion-exchange resin (Bio-Rad Laboratories, Hercules, Calif.) as per manufacturer's instructions. Determinations are made in duplicates.

CRE, SRE and NE-κ-B reporter assay: HEK293 cells (30,000 cells/well) seeded in 96-well plates are transiently transfected. In case of the CRE reporter assay, the cells are transfected with a mixture of pFA2-CREB and pFR-Luc reporter plasmid (PathDetect CREB trans-Reporting System, Stratagene, La Jolla, Calif.) or SRE-Luc (PathDetect SRE Cis-Reporting System, Stratagene, La Jolla, Calif.) and the indicated amounts of receptor DNA. Following transfection, cells are maintained in low serum (2.5%) throughout the experiments and are treated with the respective inhibitor of intracellular signaling pathways. One day after transfection, cells are treated with the respective ligands in an assay volume of 100 µl medium for 5 hrs. The assay is terminated by washing the cells twice with PBS and addition of 100 µl Luciferase® assay reagent (LucLite®, PerkinElmer, Inc., Wellesley, Mass.). Luminescence is measured in a TopCounter (Top Count NETT, Packard Instrument Co., Meriden, Conn.) for 5 sec. Luminescence values are given as relative light units (RLU).

MAP Kinase assay: COS 7 cells (seeding density 150,000 cells/well) are transfected in the assay plates. Two days after transfection, the indicated concentration of ligand are added to assay medium without any serum and incubated for 10 min at 37° C. The reaction is stopped by removing the medium and two washing steps with ice cold PBS. The cells are lysed in sample buffer and separated on 10% SDS-PAGE according to Laemmli U.K., Nature 227:680-85 (1970). Proteins are transferred onto nitrocellulose and Western blot analysis carried out using a 1:5000 dilution of mouse monoclonal antiphospho-ERK1/2 antibody (Santa Cruz Biotechnology, Inc., Santa Cruz, Calif.). Total ERK protein is determined using a 1:10000 dilution of anti-ERK antibody (Santa Cruz Biotechnology, Inc., Santa Cruz, Calif.). Blots are probed with anti-mouse horseradish peroxidase-conjugated secondary antibodies, visualized using enhanced chemiluminescence reagent (GE Healthcare, Piscataway, N.J.) and quantified by densiometric analysis. ERK1/2 phosphorylation is normalized according to the loading of protein by expressing the data as a ratio of phosphoERK1/2 over total ERK1/2. Results are expressed as percentage of the value obtained in non-stimulated mock transfected cells.

Example 5

Neuroprotective Effect of Acylated Ghrelin Splice Variant

The protective effects of ghrelin splice variant against induced cell death, cell viability, of C57Bl/6 mice primary cell culture, was analysed by trypan blue assay, an indirect method based on the dye exclusion of live cells with intact cell membrane.

Cells were treated with 50 µM $H_2O_2$ to induce cell damages and death. The neuroprotective effect of ghrelin splice variant was tested by treating the cells with either $H_2O_2$ plus 1 µM ghrelin splice variant, $H_2O_2$ plus 1 µM ghrelin or $H_2O_2$ plus both peptides. Controls samples were untreated cells. In FIG. 1, results clearly show that $H_2O_2$ treatment induced a massive cell death, the toxicity of the compound leads to 50% of the cell survival, moreover, ghrelin splice variant and ghrelin treatments, alone or in combination, seem to exert a statistically significant effective protective action against the damages produced by $H_2O_2$ in terms of cell viability compared to the negative control ($H_2O_2$). Furthermore, the efficacy of ghrelin splice variant peptide seems to be greater than ghrelin treatment, and the presence of ghrelin splice variant and ghrelin together results in a synergic activity of the two compounds.

Example 6

Patch Clamp Recordings from SN DA Neurons, Determining the Effect of Ghrelin Splice Variant on Synaptic Input Organization and Firing Rate of Nigral DA Neurons in GHSR1 Knockout Animals and Their Wild Type Littermates Brain slices preparation: Brain slices (300 µm) containing the SN, will be cut on a vibratome from 4-6 week old males (n=10 per group). Briefly, animals will be anesthetized with Nembutal (80 mg/kg) and then decapitated. The brains will be rapidly removed and immersed in cold (40 C) oxygenated bath solution (containing (mM): NaCl 150, KCl 2.5, CaCl2 2, MgCl2 2 Hepes 10, and glucose 10, pH 73 with NaOH). After being trimmed to contain only the SN, slices will be transferred to a recording chamber where they are constantly perfused with bath solution at 2 ml/min. DA neurons in the SN are identified by presence of a large Ih current (>100 pA) evoked by hyperpolarizing voltage steps from −50 to −120 mV for 2 s (22). This approach identifies dopaminergic cells with >90% accuracy. In brain slices, whole-cell current clamp will be used to observe spontaneous action potentials. Slices will be maintained at 330 C and perfused continuously with ASCF (bubbled with 5% CO2 and 95% O2) containing (in mM): NaCl, 124; KCl, 3; CaCl2, 2; MgCl2, 2; NaH2PO4, 1.23; NaHCO3, 26; glucose, 10; pH 7.4 with NaOH. Ghrelin Splice Variant will be applied to the recording chamber via bath application.The pipette solution containes (mM): Gluconic Acid 140, CaCl2, MgCl2 2, EGTA 1, HEPES 10, Mg-ATP 4, and Na2-GTP 0.5, pH 7.3 with KOH. To further explore the mechanism of Ghrelin Splice Variant-mediated effect on action potentials in DA neurons, we will analyze the effect of Ghrelin Splice Variant on action potential frequency either in the presence of ionotropic glutamate receptor antagonists CNQX (10 µM) and APS (50 µM) in all solutions, or in the presence of bicuculine (30 □M; to block diminish GABA effects) in all solutions. Analysis: All data will be sampled at 3-10 kHz and littered at 1-3 kHz with an Apple Macintosh computer using Axograph 4.9 (Axon Instruments). Electrophysiological data will be analyzed with Axograph 4.9 (Axon Instruments) and plotted with Igor Pro software (WaveMetrics, Lake Oswego, Oreg., USA). To complement, the electron microscopic measurements of synapses, we will also analyze mEPSC and mIPSC of SN DA neurons. Mice (C57BL/J6; n=10) between the ages of 4-6 weeks of age will be injected with Ghrelin Splice Variant (30 μg in 0.3 ml) or vehicle ip at 09:00 hrs. Two hours later, animals will be sacrificed under neinbutal anesthesia and their brains collected as described above. For the recording of mEPSCs and IPSCs, SN DA cells will be patched with pipettes with a tip resistance of 4-6 MΩ and partially compensated by the amplifier. The pipette will be filled with a solution containing the following (mM): KMeSO, 145 (mEPSC) or KCL, 145 (mIPSC); MgCl2, 2; HEPES, 10; Mg-ATP, 2.; Nat-GTP, 0.3; and KOH to adjust pH to 7.3. mEPSC recordings will be achieved under the prescence of TTX and bicucullin, whereas mIPSC will be monitored under the presence of TTX, AP5 and CNQX. The frequency and amplitude of mEPSC and IPSC will be recorded as described previously. Differences in the frequency of mEPSCs and mIPSCs of DA cells from Ghrelin Splice Variant and saline treated animals will be compared using unpaired t-tests with the critical level set at α=0.05).

Figure 2:
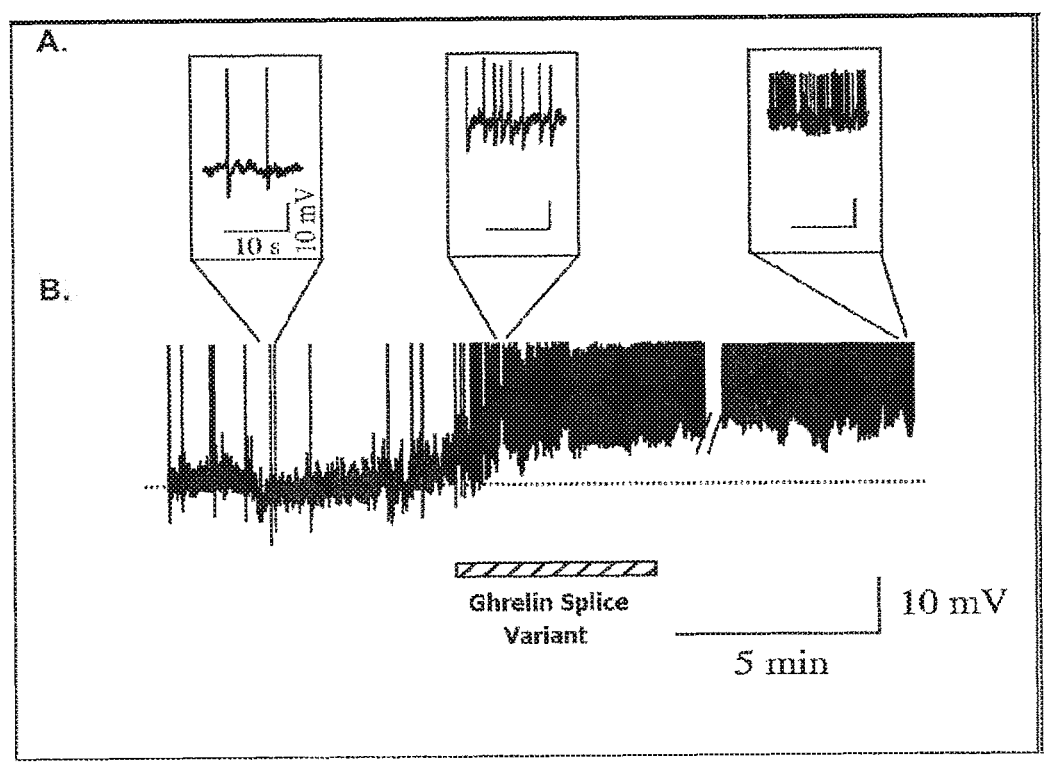
FIG. 2. Ghrelin Splice Variant Increases Action Potential Generation in SNpc DA Neurons in Mice. Ghrelin Splice Variant (1 μM) was applied to the recording chamber via bath application. Ghrelin Splice Variant induced a significant depolarization (about 10 mV) and increment in AP firing in this DA neuron. The effect of Ghrelin Splice Variant lasted for at 20 minutes after washout. A. Raw traces recorded before (Control), during (Ghrelin Splice Variant), and after (Washout) application of Ghrelin Splice Variant. B. Time course of Ghrelin Splice Variant-induced increase in frequency of action potential (FAP).

In FIG. 2 it is clear that Ghrelin splice variant induced a significant depolarization (about 10 mV) and an increment in action potential firing in this dopaminergic neuron. The effect of the Ghrelin splice variant lasted for at least 20 minutes after washout indicating that the Ghrelin splice variant induces plasticity.

Figure 3:
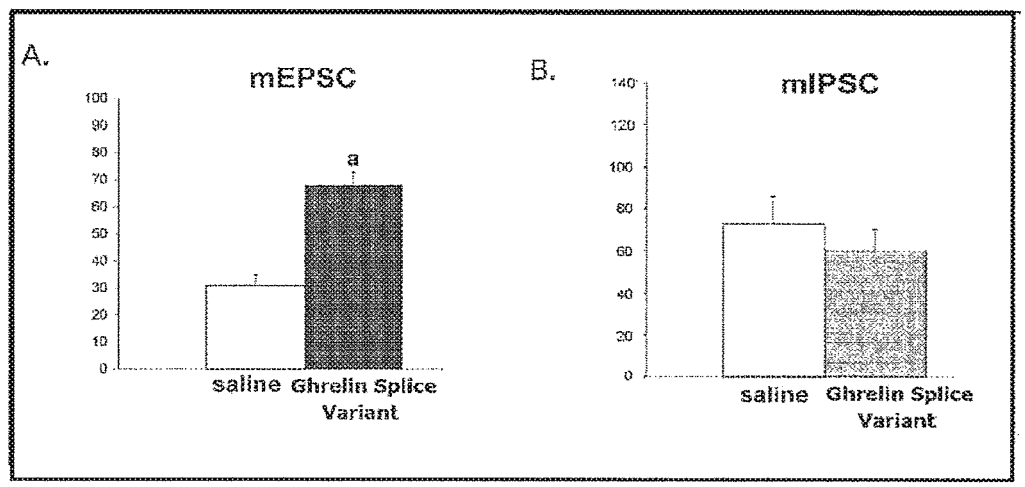
FIG. 3. Ghrelin Splice Variant Elevates the Frequency of mESPCS in WT Mice. A. Significant elevation in the frequency of mEPSCs compared with saline control after treatment with Ghrelin Splice Variant (67.2+3.1. (n=6) versus Saline 30.35+2.5 (n=8). B. Conversely, a significant decrease in the frequency of mIPSCs was triggered by Ghrelin Splice Variant (Ghrelin Splice Variant: 60.5+8.9 (n=6) versus Saline 72.5+11.2 (n=5)).

In FIG. 3. As can be seen in FIG. 3 there was a significant elevation in the frequency of mEPSCs compared with saline control after treatment with Ghrelin splice variant in WT mice: Ghrelin splice variant (67.2+3.1 (n=6) versus Saline 30.35+2.5 (n=8)). Conversely, a significant decrease in the frequency of mIPSCs was triggered by Ghrelin splice variant: (Ghrelin splice variant: 60.5+8.9 (n=6) versus Saline 72.5+11.2 (n=5)). N=number of cells recorded.

Figure 4:
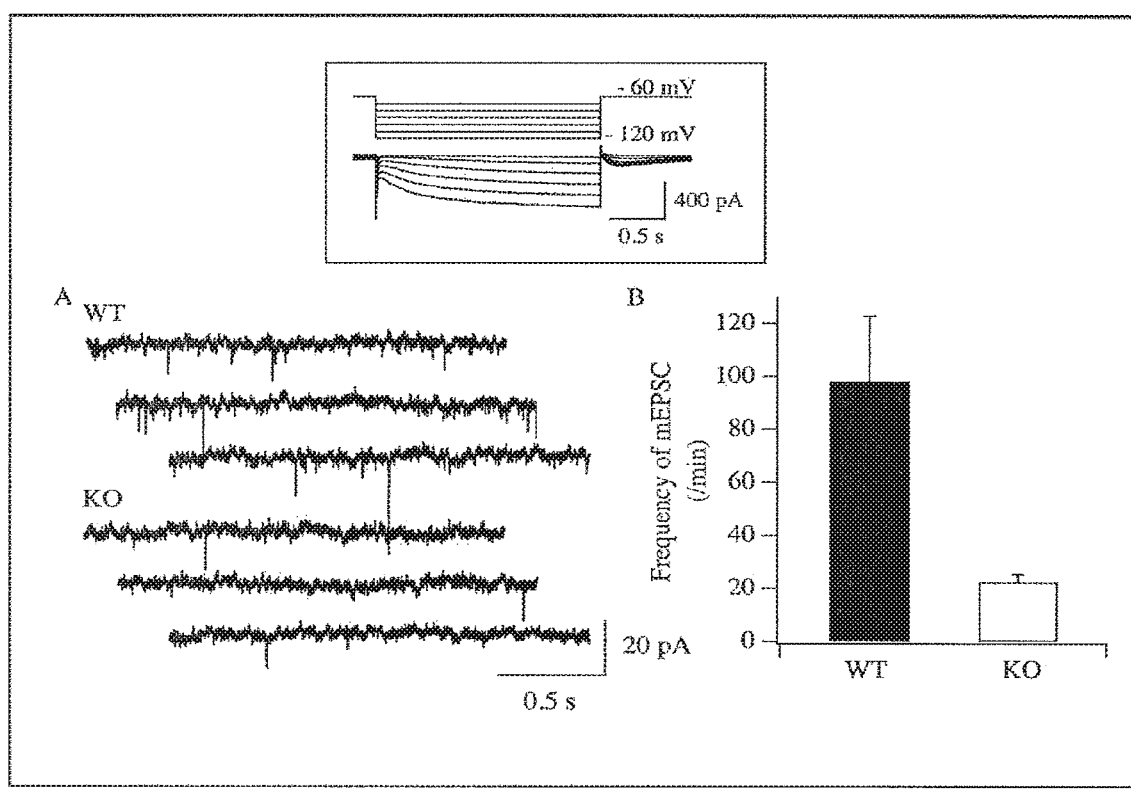
FIG. 4. of Ghrelin Splice Variant on Firing Rate of SNpc DA Neurons in GHSR1a KO mice and their WT Littermates. In WT animals Ghrelin Splice Variant (1 μM)—induced mEPSC frequency of 98.1+/−24.7 per min (n=31) and 27.3+/2.8 per min (n=9) in GHSR-KO mice indicating the involvement of GHSR-mediated effects of Ghrelin Splice Variant on SN neurons. The raw traces of mEPSCs recorded in the presence of TTX (0.5 μM) and bicuculline (30 μM) from WT and KO mice are shown in A. The mean frequency of mEPSC for WT and KO mice are shown in B. H current was induced with voltage steps from −60 mV to −120 mV to identify DA neurons in the SNC as shown in the box.
Figure 5:
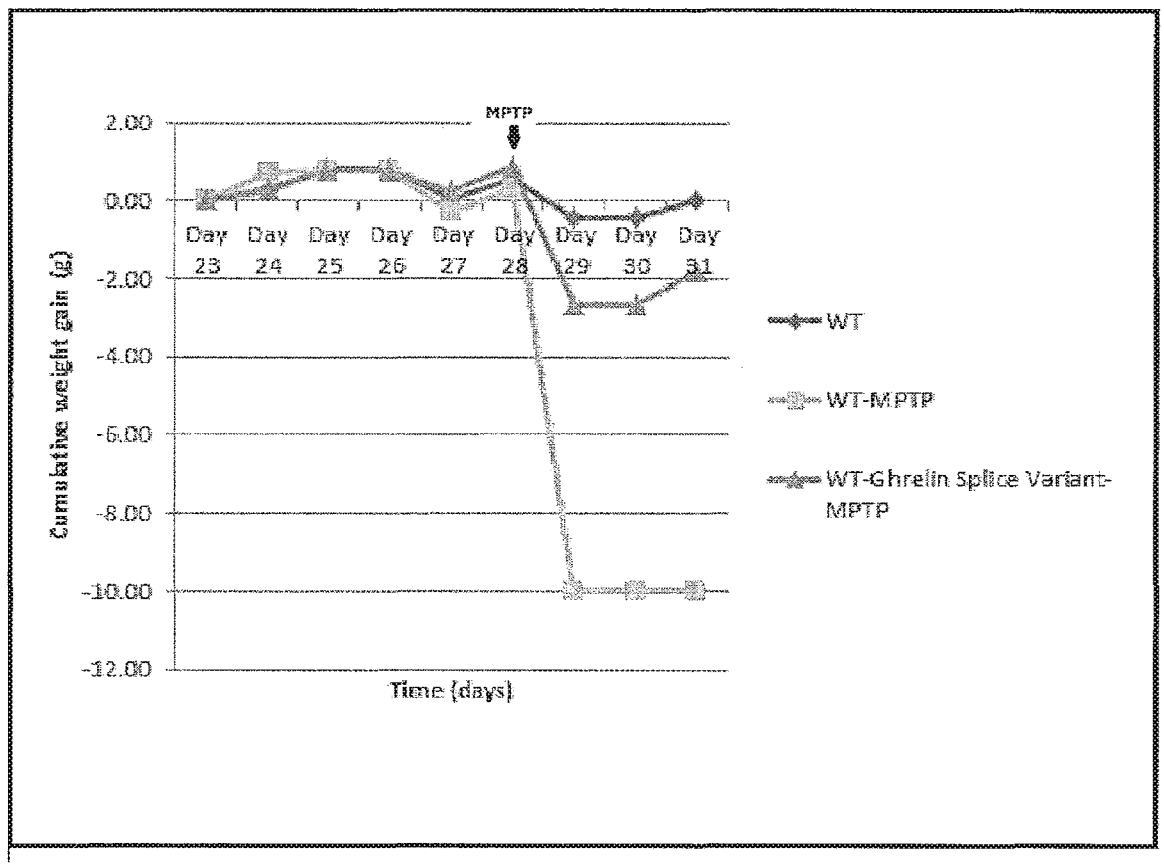
FIG. 5. Effect of Ghrelin Splice Variant on Cumulative Weight Gain of MPTP and Vehicle Treated Mice. Ghrelin Splice Variant or vehicle was be administered once-a-day immediately before the dark phase, and food was removed overnight starting seven days prior to MPTP challenge and continued until end-point day 10 after MPTP. Body weight was monitored daily in all mice administered Ghrelin Splice Variant or Vehicle. Ghrelin Splice Variant treated group managed to recover after the MPTP treatment while most of the animals in the Vehicle treated group died.
Figure 6:
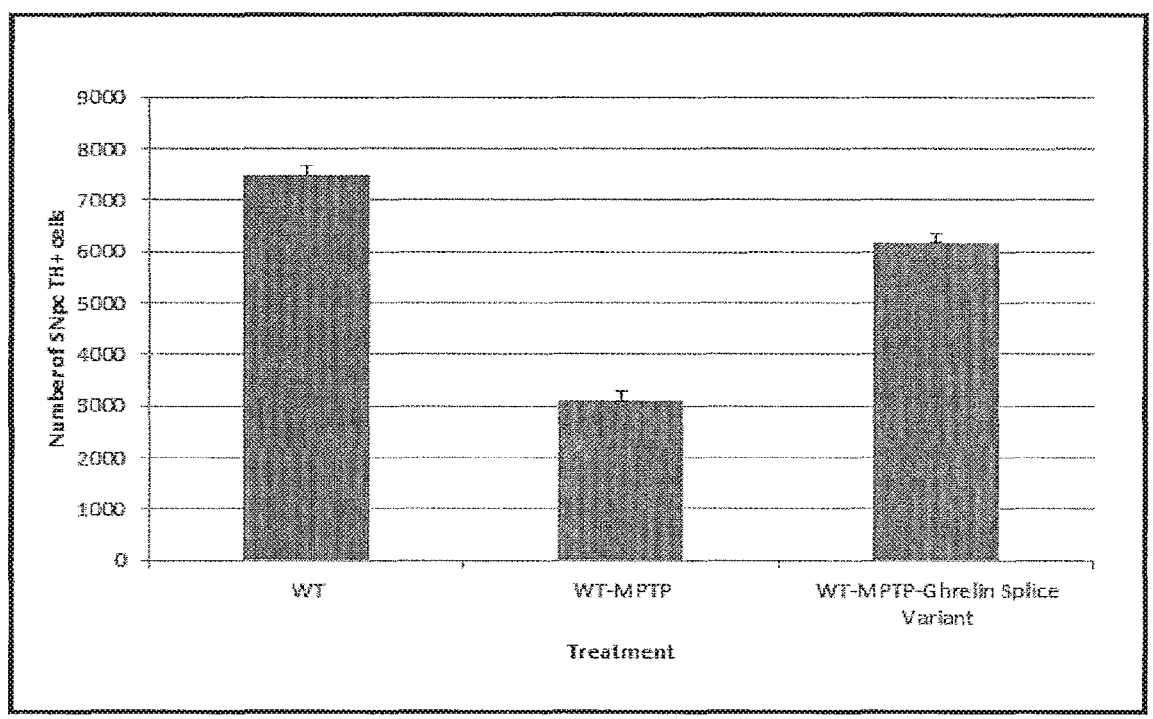
FIG. 6. Ghrelin Splice Variant attenuates MPTP-induced nigrostriatal PA damage. Ghrelin Splice Variant or vehicle were administered once-a-day immediately before the dark phase, and food was removed overnight starting seven days prior to MPTP challenge and continued until end-point day 10 after MPTP. Note the significant loss of DA neurons in wt mice treated with MPTP compared with Ghrelin Splice Variant MPTP-treated mice and the untreated control group.

In FIG. 4. mEPSC recordings were taken in the presence of tetrodotoxin (TTX) and bicucullin in GHSR1a knockout mice and their WT littermates'. The frequency and amplitude of mEPSCs was determined. Ghrelin splice variant induced mEPSC frequency in WT animals was 98.1+/−24.7 per min (n=31) and Ghrelin splice variant induced mEPSC frequency in GESR1a knockout mice was 27.3+/−2.8 per min (n=9) (N=number of cells recorded). These results indicate the involvement of GHSR1a-mediated effects of Ghrelin splice variant on SN neurons.

Example 7

Altering MPTP-Induced DA Cell Degeneration and Motor Dysfunctions by Ghrelin Splice Variant in Mice (n=10 Per Group, Ghrelin Splice Variant Treatment in a Mouse Model of Parkinson's Disease In the MPTP model, the bilateral dopaminergic neuronal death of the substantia nigra and dopamine depletion of the striatum is created by i.p. injection of MPTP. Experimental groups:

Group 1: 10 Sham-mice treated with vehicle (10 ml/kg) once-a-day starting day-7 and continuing until the end of the study day 10

Group 2: 10 MPTP-mice treated with vehicle (10 ml/kg) once-a-day starting day-7 and continuing until the end of the study day 10

Group 3: 10 MPTP-mice treated with Ghrelin SplicVariant (10 nmol) once-a-day starting day-7 and continuing until the end of the study day 10

Ghrelin Splice Variant or vehicle was administered once-a-day immediately before the dark phase, and food and food were removed overnight starting seven days prior to MPTP challenge and continued until end-point day 10 after MPTP. Striatal levels of dopamine (DA), 3,2-dihydroxyphenylacetic acid (DOPAC) and homovanillic acid (HVA) are evaluated 10 days after the injection of MPTP with HPLC. In addition, the selective damage to dopaminergic neurons in the SNc is evaluated with tyrosine hydroxylase (TH) immunoreactivity. Food intake and body weight were monitored daily in all mice administered Ghrelin Splice Variant.

Example 8

Effect of Subcutaneous Administration of Acylated Ghrelin Spice Variant on GH Release Acylated ghrelin splice variants (20 μg) or the Vehicle (1.6% mannitol) were administered by a subcutaneous bolus injection (Corresponding to 0.3 μmol/kg) to 5 mice each. Blood was sampled 10 and 20 min after injection. Serum samples were stored at −70° C. and analyzed by the RAT/MOUSE GROWTH HORMONE ELISA KIT 96-Well Plate (Cat. EZRMGH-45K) (Millipore Corporation, Billerica, Mass., USA).

Results: The serum and brain growth hormone concentration 10 minutes after subcutaneous administration of acylated ghrelin splice variant or the Vehicle was 2-14-fold higher in the ghrelin splice variant group in comparison to the vehicle group.

Example 9

Pharmacokinetics of Acylated Ghrelin Splice Variant Range Finder into Mice

Subcutaneous administration of ghrelin splice variants was performed at three dose levels of 0.5, 2.5 and 10 mg/kg corresponding to concentrations of 0.1, 0.5 and 2 mg/ml, respectively, and at a constant volume dosage of 5 ml/kg. Intravenous injection was performed at one dose level of 0.5 mg/kg corresponding to a concentration of 0.1 mg/ml and a constant volume dosage of 5 ml/kg as well. The study comprised 9 male and 9 female Sprague-Dawley™ (SD™) rats per dose level and route of administration.

Bleeding sampling design was confined to 9 bleeding time points for each dose level: pre-dosing, 5, 15, 30, 60 and 90 min, 3, 5 and 24 hrs, post-dosing. Each group was divided into 3 sub-groups, each being assigned 3 specific bleeding time points, in order to receive 3 individual samples/time point/group (total of 27 individual samples/group). Mean group body weight values at initiation of the study were similar among all groups and did not exceed ±20% of the mean weight per gender. Whole blood samples were kept on ice from the time of blood collection until the time of centrifugation. The obtained plasma samples were flash frozen in liquid nitrogen and kept on dry ice until removal to −70° C.

Concentrations of the Test Item in plasma were determined by LC/MS/MS (liquid chromatography/mass spectrometry/mass spectrometry). Pharmacokinetic analysis of Ghrelin Splice Variant was based on mean plasma concentration time profiles for each dose group as obtained by Non-compartmental Pharmacokinetic analysis, generated by the use of the computer software: "PK Solutions 2.0" (Summit Research Services, Colo., USA).

Pharmacokinetic analysis for the SC route showed that $AUC_{0-\infty}$ values were similar for males and females administered the low dose (6.1 and 5.2 mcg·min/ml, respectively) and mid close (18.8 and 20.8 mcg·min/ml, respectively). At the high dose, AUC values of the females were substantially lower (49.1 mcg·min/ml) than that of males (79.2 mcg·min/ml). $T_{max}$ occurred at 5 minutes post-dosing for all dose groups. $T_{1/2}$ values ranged from 17.4 to 26.4 minutes for male rats and 10.7 to 28.9 minutes for female rats.

Example 10

Examples of Diaries/Questionnaires Assessing Patient Quality of Life

A) EORTC QLQ-C30 (Aaronson et al., J. Natl. Cancer Inst. 85: 365-76 (1993)), see the National Institutes of Health website and see, for example, a specimen of EORTC QLQ-C30 (version 3.0), available on the EORTC website and incorporated herein by reference.

We are interested in information regarding you and your health. Please answer the follow questions by ticking off the number that applies best to you. There are no "right" or "wrong" answers. This information will be treated with confidentiality.

Questions: See specimen of EORTC QLQ-C30 (version 3.0), available on the EORTC website and incorporated herein by reference).

Example 11

Examples of Suitable Formulations for Preparing Pharmaceutical Compositions for Use in the Present Disclosure 4% Mannitol Solution is prepared by dissolving D-Mannitol in Water for injection to achieve final concentration of 40 mg/ml. Ghrelin Splice Variant Stock Solution is prepared by dissolving ghrelin splice variant in TFA salt or in Acetate (5 mg) in 10 ml of 4% Mannitol solution, divided into aliquots and kept frozen (−70° C.) until the time of use.

Ghrelin Splice Variant Dosing Solution: On each day of dosing, the required amount of each test item is thawed and diluted with Physiological Saline to a concentration of 0.2 mg/ml.

Control Item Dosing Solution: Prepared on each day of dosing, by diluting 4% Mannitol Solution with Physiological Saline at the same ratio as the Ghrelin Splice Variant Dosing Solution.

Patients: Patients with documented neuronal damage and/or neurodegenerative disease and documented parkinson's disease or alzheimer's disease.

Efficacy of ghrelin splice variant action will be assessed according to clinical assessments:

(1) Effect of Ghrelin Splice Variant on change in motor, mood, and cognitive function
(2) Parkinson's disease-specific assessments: Parts I, II, and III of the revised Movement Disorders Society Unified Parkinson Disease Rating Scale (MDS-UPDRS), Geriatric Depression Scale (GDS), The Montreal Cognitive Assessment (MoCA)
(3) Acute Food intake: Dietician-assessed food intake during the infusion.
(4) Chronic Food intake: A daily report of the amount of food consumed during the day, and assessment of the pleasantness related to the food intake. This will be validated by urine nitrogen excretion, based on 4 day diet diary.
(5) Body-weight: Standard and calibrated scale will be used at the clinic.
(6) Resting energy expenditure (REE) is a very important measurement, since it is affected both by the state of the disease and the body size.
(7) Exercise test: Actigraph is used according to standard protocol described on the Actigraph website.
(8) Health-related QOL using standard forms as described supra.
(9) Para-clinical assessments:
  (i) Nitrogen excretion in the urine: 24 h urine collection should be used as validation of the reported food intake.
  (ii) Plasma glucose, plasma FFA, plasma triglycerides, plasma glycerol and plasma amino acids: Plasma substrates measured to ensure the reported food intake is in accordance with the absorbed amount of food intake.
  (iii) Lean body mass and fat mass assessed by TSF thickness and mid-arm circumference as a measurement of body composition.
  (iv) Total body fat (and fat free mass) will be assessed DEXA scan, using software 1.31 for the lunar DPX-L (Scanexport Medical, Helsingborg, Sweden).
  (v) Plasma Leptin: Leptin is produced by and secreted from the fat cell. The plasma level of leptin gives an estimate of the total fat cell burden.
  (vi) Plasma Ghrelin: The basal ghrelin level tends to be increased in cachectic patients.
  (vii) Plasma-GH: In previous studies, GH has been measured as a control for the effect of ghrelin administration (Enomoto M. et al., Clin. (Lond), 105:431-35 (2003)).
  (viii) IGF-I: A single determination of IGF-I summarizes 24 h of GH secretion. This has been demonstrated in healthy volunteers where levels of circulating IGF-I have been shown to correlate with spontaneous GH secretion (Rose S. R. et al., N. Engl. J. Med. 319:201-07 (1988)). IGF-I may also increase independently of GH increase by improved nutritional status.
  (ix) IGFBP-3: One of the carrier proteins for IGF-I. It increases in parallel with IGF-I but with a slower response rate.
  (x) Albumin: is an indicator of nutritional status.
  (xi) Prealbumin: indicator of nutritional status, with quicker response to alterations than albumin.
  (xii) Cortisol: Ghrelin administration has been shown to increase the serum cortisol level (Broglio F. et al., J. Endocrinol. Metab. 88:1537-42 (2003)). Corticosteroids have been shown to have a significant anti-nausea effect and to improve asthenia and pain control, which may be beneficial for the cachectic cancer patient. However, cortisol has never been shown to increase weight in cachectic cancer patients.

(xiii) CRP and ESR: Acute phase proteins and ESR are often good indicators of systemic inflammation related to the cancer process (Inui A., C A Cancer J. Clin. 52:72-91 (2002)).

Example 12

Treatment of Patients Parkinson's Disease

Thirty-two Parkinson's Disease (PD) patients will be enrolled in four, 8-person dose-escalating cohorts. Subjects in each cohort will be randomized 6:2 (active:placebo) to receive subcutaneous injections of Dln101 or placebo once daily for 7 consecutive days. Safety parameters will be assessed on Day 1 to Day 8 and Day 15. The next cohort will begin dosing approximately 7 days after the Day 15 safety parameters have been reviewed for the previous cohort by the study investigators and medical monitor. Blood will be drawn for determination of anti-Dln101 antibodies at Day 22.

Subjects will have a diagnosis of probable PD, based on Gelb criteria, within the last 5 years with Hoehn and Yahr stage 1-3 (not severely disabled). Use of levodopa and dopamine agonist therapy will be permitted. Patients will receive subcutaneous administration of a single dose of 10, 50, 100, or 150 µg/kg of Ghrelin Splice Variant or placebo. The protocol will start at 08.00 hours after an overnight fast. A 22-gauge catheter will be inserted into an antecubital vein for blood sampling. After an equilibration period of 30 min, ghrelin splice variant (10 µg/k placebo (0.9% saline) will be administered subcutaneously.

Investigational treatment: Ghrelin splice variant will be available in GMP-quality in prepared vials of 10 µg/kg, from BACHEM AG, Switzerland or NeoMPS Inc., USA. Placebo consists of normal saline (or the vehicle used to dissolve study substance), which will be provided by a hospital pharmacy. Ghrelin splice variant is dissolved in saline, and a dose of 10 µg/kg ghrelin splice variant will be administered to the patient.

Assessments of Efficacy:

(1) Effect of Ghrelin Splice Variant on change in motor, mood, and cognitive function (2) Quality of life: will be assessed using the EORTC-QLQ-C30 questionnaire (see example 9).

(3) Nutritional intake and food preferences: food intake measurement will be by percentage calculation of food products consumed at each meal by the patient, the clinical dietician will assess the food preferences as part of their routine assessments.

(4) Food pleasantness: will be assessed after lunch using visual analogue scales, following established anchors.

(5) Perceived appetite, hunger, nausea and satiety: will be assessed in the morning, before infusion, and before and after lunch using visual analogue scale, following established anchors. Applicant will also apply a shortened ad hoc taste questionnaire.

(6) Growth hormone (GH): since GH reflects directly the biological function of ghrelin, with a rapid increase of GH after ghrelin injections, Applicant will also monitor GH levels at the same time points as ghrelin. A standard ghrelin assay will be used.

(7) Body composition: body compositions will be assessed by BMI, bioimpedance analysis and dual photon absorptiometry/dual energy x-ray absorptiometry (DEXA).

(8) Albumin and transferrin levels will be determined as parameters for nutritional status.

(9) Cardiovascular autonomic function: for the screening of autonomic disorders, a 20 minute Holter EKG will be performed, and the SDNN value determined.

(10) Parkinson's disease-specific assessments: Parts I, II, and III of the revised Movement Disorders Society Unified Parkinson Disease Rating Scale (MDS-UPDRS), Geriatric Depression Scale (GDS), The Montreal Cognitive Assessment (MoCA)

The invention claimed is:

1. A method for enhancing resistance of neurons to cellular stress, comprising administering to a subject suffering from neuronal damage a ghrelin splice variant-like compound consisting of the amino acid sequence of SEQ ID NO:4 to enhance resistance of neurons to cellular stress.

2. A method in accordance with claim 1, wherein said subject suffering from neuronal damage is one having a neurodegenerative disease.

3. A method in accordance with claim 2, wherein said subject suffering from neuronal damage is one suffering from Parkinson's disease.

4. A method in accordance with claim 2, wherein said subject suffering from neuronal damage is one suffering from Alzheimer's disease.

5. The method of claim 1, wherein the ghrelin splice variant-like compound is conjugated to a polymer molecule.

6. The method of claim 5, wherein the polymer molecule is selected from the group consisting of polyalkylene oxide, polyalkylene glycol, poly-vinyl alcohol, poly-carboxylate, poly-(vinylpyrrolidone), polyethylene-co-maleic acid anhydride, polystyrene-co-maleic acid anhydride, and dextran.

7. The method of claim 1, wherein the ghrelin splice variant-like compound is modified with a chemically reactive group.

8. The method of claim 7, wherein the chemically reactive group is selected from the group consisting of N-hydroxy-succinimide, N-hydroxy-sulfosuccinimide, maleimide-benzoyl-succinimide, gamma-maleimido-butyryloxy succinimide ester, and maleimidopropionic acid.

9. The method of claim 1, wherein the ghrelin splice variant-like compound is modified with a C1-C35 acyl group.

10. The method of claim 1, wherein the ghrelin splice variant-like compound is acylated at position 3 of SEQ ID NO:4.

* * * * *